(12) United States Patent
Altmann et al.

(10) Patent No.: US 7,112,589 B2
(45) Date of Patent: Sep. 26, 2006

(54) CYSTEINE PROTEASE INHIBITORS WITH 2-CYANO-4-AMINO-PYRIMIDINE STRUCTURE AND CATHEPSIN K INHIBITORY ACTIVITY FOR THE TREATMENT OF INFLAMMATIONS AND OTHER DISEASES

(75) Inventors: Eva Altmann, Reinach (CH); Kenji Hayakawa, Hyogo (JP); Genji Iwasaki, Ibaraki (JP)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/487,741

(22) PCT Filed: Aug. 29, 2002

(86) PCT No.: PCT/EP02/09661

§ 371 (c)(1),
(2), (4) Date: Feb. 24, 2004

(87) PCT Pub. No.: WO03/020278

PCT Pub. Date: Mar. 13, 2003

(65) Prior Publication Data

US 2004/0249153 A1 Dec. 9, 2004

(30) Foreign Application Priority Data

Aug. 30, 2001 (GB) .................. 0121024.4
Aug. 30, 2001 (GB) .................. 0121026.9

(51) Int. Cl.
*C07D 239/42* (2006.01)
*A61K 31/506* (2006.01)

(52) U.S. Cl. .................. 514/252.14; 514/256; 544/326; 544/328; 544/329

(58) Field of Classification Search .............. 544/326, 544/328, 329; 514/252.14, 256
See application file for complete search history.

(56) References Cited

U.S. PATENT DOCUMENTS

| 3,202,499 A | 8/1965 | Knusli | 71/2.5 |
| 4,220,770 A | 9/1980 | Gass | 544/208 |
| 2003/0032647 A1 | 2/2003 | Yamada et al. | 514/255.05 |

FOREIGN PATENT DOCUMENTS

| CA | 2328438 | 10/1999 |
| CH | 437911 | 11/1960 |
| DE | 198 17 459 | 10/1999 |
| GB | 1308811 | 3/1973 |
| WO | WO 97/09315 | 3/1997 |
| WO | WO 97/28128 | 8/1997 |
| WO | WO 01/19816 | 3/2001 |
| WO | WO 01/83460 | 11/2001 |
| WO | WO 01/96327 | 12/2001 |
| WO | WO 2004/000819 | 12/2003 |
| WO | WO 2004/000843 | 12/2003 |

OTHER PUBLICATIONS

Wang et al., Cathepsin K inhibitor—polymer conjugates: potential drugs for the treatment of osteoporosis and rheumatoid arthritis, International Journal of Pharmaceutics, 277, pp. 73-79, 2004.*
Simone, Oncology: Introduction, Cecil Textbook of Medicine, 20th edition, vol. 1, pp. 1004-1010, 1996.*
Besson, Rees, Cottenceau and Pons, "Antimicrobial Evaluation of 3,1-Benzoxazin-4-ones, 3,1-Benzothiazin-4-ones, 4-Alkoxyquinazolin-2-carbonitriles and N-Arylimino-1,2,3,-dithiazoles", *Bioorg Med Chem Lett*, vol. 6, No. 19, pp. 2343-2348 (1996).
Caravatti, Rahuel, Gay and Furet, "Structure-based Design of a Non-peptidic Antagonist of the SH2 Domain of GRB2", *Bioorg Med Chem Lett*, vol. 9, No. 14, pp. 1973-1978 (1999).
Chang and Kim, "A Facile Synthesis of N-Arylcyanofomamidoximes, 4-Aryl-3-cyano-1,2,4-oxadiazin-5(6H)-ones, 2-Cyanoquinazoline-3-oxides, and 2-Cyanoquinazolines via 5-Arylmino-4-cholor-5H-1,2,3-dithiazoles", Heterocycles, vol. 51, No. 11, pp. 2653-2666 (1999)—see CAPLUS Abstract No. 1999:710017.
Mori, Kawakami and Hashida, "Synthesis and Reactions of Cyan-1,3,5-triazines", *Nippon Kagaku Kaishi*, vol. 4, pp. 396-400 (1990)—see CAPLUS Abstract No. 1990:515257.
Yamada, Matsuki, Kenji and Kikkawa, "Preparation of Heterocyclic Compounds as Phosphodiesterase V (PDE V) Inhibitors", Japan (2001)—CAPLUS Abstract No. 2001:816647 [English equivalent of WO 01/83460].
On Line EPO Database Search for EP 0 850 228, Mar. 13, 1997 and WO 97/09315, Mar. 13, 1997.

* cited by examiner

*Primary Examiner*—Deepak Rao
(74) *Attorney, Agent, or Firm*—Oona A. Jackson; Edward J. Wilusz, Jr.

(57) ABSTRACT

The invention provides compounds of formula I or a pharmaceutically acceptable salt or ester thereof (I), wherein the symbols have meaning as defined, which are inhibitors of cathepsin K and find use pharmaceutically for treatment of diseases and medical conditions in which cathepsin K is implicated, e.g. various disorders including inflammation, rheumatoid arthritis, osteoarthritis, osteoporosis and tumors

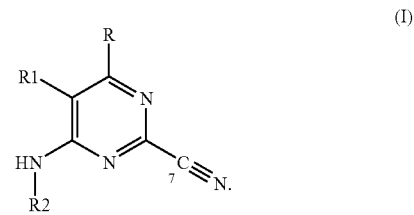

(I)

9 Claims, No Drawings

CYSTEINE PROTEASE INHIBITORS WITH 2-CYANO-4-AMINO-PYRIMIDINE STRUCTURE AND CATHEPSIN K INHIBITORY ACTIVITY FOR THE TREATMENT OF INFLAMMATIONS AND OTHER DISEASES

This invention relates to inhibitors of cysteine proteases, in particular to heteroaryl nitrile cathepsin K inhibitors and to their pharmaceutical use for the treatment or prophylaxis of diseases or medical conditions in which cathepsin K is implicated.

Cathepsin K is a member of the family of lysosomal cysteine cathepsin enzymes, e.g. cathepsins B, K, L and S, which are implicated in various disorders including inflammation, rheumatoid arthritis, osteoarthritis, osteoporosis, tumors (especially tumor invasion and tumor metastasis), coronary disease, atherosclerosis (including atherosclerotic plaque rupture and destabilization), autoimmune diseases, respiratory diseases, infectious diseases and immunologically mediated diseases (including transplant rejection).

Accordingly the present invention provides a compound of formula I, or a pharmaceutically acceptable salt or ester thereof

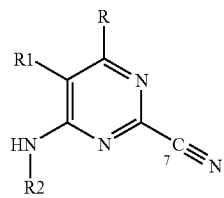

I wherein

R is H, —R4, —OR4 or NR3R4, wherein R3 is H, lower alkyl or $C_3$ to $C_{10}$ cycloalkyl, and R4 is lower alkyl or $C_3$ to $C_{10}$ cycloalkyl, and wherein R3 and R4 are independently, optionally substituted by halo, hydroxy, lower alkoxy, CN, $NO_2$, or optionally mono- or di-lower alkyl substituted amino;

R1 is —CO—NR5R6, —NH—CO—R5, —$CH_2$—NH—C(O)—R5, —CO—R5, —S(O)—R5, —$S(O)_2$—R5, —$CH_2$—CO—R5 or —$CH_2$—NR5R6, wherein R5 is aryl, aryl-lower alkyl, $C_3$–$C_{10}$cycloalkyl, $C_3$–$C_{10}$cycloalkyl-lower alkyl, heterocyclyl or heterocyclyl-lower alkyl, R6 is H, aryl, aryl-lower alkyl, aryl-lower-alkenyl, $C_3$–$C_{10}$cycloalkyl, $C_3$–$C_{10}$cycloalkyl-lower alkyl, heterocyclyl or heterocyclyl-lower alkyl, or wherein R5 and R6 together with the nitrogen atom to which they attached are joined to form an N-heterocyclyl group, wherein N-heterocyclyl denotes a saturated, partially unsaturated or aromatic nitrogen containing heterocyclic moiety attached via a nitrogen atom thereof having from 3 to 8 ring atoms optionally containing a further 1, 2 or 3 heteroatoms selected from N, NR7, O, S, S(O) or $S(O)_2$ wherein R7 is H or optionally substituted (lower alkyl, carboxy, acyl (including both lower alkyl acyl, e.g. formyl, acetyl or propionyl, or aryl acyl, e.g. benzoyl), amido, aryl, S(O) or $S(O)_2$), and wherein the N-heterocyclyl is optionally fused in a bicyclic structure, e.g. with a benzene or pyridine ring, and wherein the N-heterocyclyl is optionally linked in a spiro structure with a 3 to 8 membered cycloalkyl or heterocyclic ring wherein the heterocyclic ring has from 3 to 10 ring members and contains from 1 to 3 heteroatoms selected from N, NR6, O, S, S(O) or $S(O)_2$ wherein R6 is as defined above), and wherein heterocyclyl denotes a ring having from 3 to 10 ring members and containing from 1 to 3 heteroatoms selected from N, NR7, O, S, S(O) or S(O) wherein R7 is as defined above), and wherein R5 and R6 are independently, optionally substituted by one or more groups, e.g. 1–3 groups, selected from halo, hydroxy, oxo, lower alkoxy, CN or $NO_2$, or optionally substituted (optionally mono- or di-lower alkyl substituted amino, lower-alkoxy, aryl, aryl-lower alkyl, N-heterocyclyl or N-heterocyclyl-lower alkyl (wherein the optional substitution comprises from 1 to 3 substituents selected from halo, hydroxy, lower alkoxy, lower alkoxy-lower alkyl, lower alkoxy-carbonyl, CN, $NO_2$, N-heterocyclyl or N-heterocyclyl-lower alkyl, or optionally mono- or di-lower alkyl substituted amino;

R2 is is independently H, or optionally substituted (lower alkyl, aryl, aryl-lower alkyl, $C_3$–$C_{10}$cycloalkyl, $C_3$–$C_{10}$cycloalkyl-lower alkyl, heterocyclyl or heterocyclyl-lower alkyl), and wherein R2 is optionally substituted by halo, hydroxy, oxo, lower alkoxy, CN, $NO_2$, or optionally mono- or di-lower alkyl substituted amino.

Above and elsewhere in the present description the following terms have the following meanings.

Halo or halogen denote I, Br, Cl or F.

The term "lower" referred to above and hereinafter in connection with organic radicals or compounds respectively defines such as branched or unbranched with up to and including 7, preferably up to and including 5 and advantageously one, two or three carbon atoms.

A lower alkyl group is branched or unbranched and contains 1 to 7 carbon atoms, preferably 1–5 carbon atoms. Lower alkyl represents; for example, methyl, ethyl, propyl, butyl, isopropyl isobutyl, tertiary butyl or neopentyl (2,2-dimethylpropyl).

Halo-substituted lower alkyl is $C_1$–$C_7$lower alkyl substituted by up to 6 halo atoms.

A lower alkoxy group is branched or unbranched and contains 1 to 7 carbon atoms, preferably 1–4 carbon atoms. Lower alkoxy represents for example methoxy, ethoxy, propoxy, butoxy, isopropoxy, isobutoxy or tertiary butoxy.

A lower alkene, alkenyl or alkenyloxy group is branched or unbranched and contains 2 to 7 carbon atoms, preferably 2–4 carbon atoms and contains at least one carbon—carbon double bond. Lower alkene lower alkenyl or lower alkenyloxy represents for example vinyl, prop-1-enyl, allyl, butenyl, isopropenyl or isobutenyl and the oxy equivalents thereof.

A lower alkyne, alkynyl or alkynyloxy group is branched or unbranched and contains 2 to 7 carbon atoms, preferably 2–4 carbon atoms and contains at least one carbon—carbon triple bond. Lower alkyne or alkynyl represents for example ethynyl, prop-1-ynyl, propargyl, butynyl, isopropynyl or isobutynyl and the oxy equivalents thereof. In the present description, oxygen containing substituents, e.g. alkoxy, alkenyloxy, alkynyloxy, carbonyl, etc. encompass their sulphur containing homologues, e.g. thioalkoxy, thioalkenyloxy, thioalkynyloxy, thiocarbonyl, sulphone, sulphoxide etc.

Aryl represents carbocyclic or heterocyclic aryl.

Carbocyclic aryl represents monocyclic, bicyclic or tricyclic aryl, for example phenyl or phenyl mono-, di- or tri-substituted by one, two or three radicals selected from lower alkyl, lower alkoxy, aryl, hydroxy, halogen, cyano, trifluoromethyl, lower alkylenedioxy and oxy-$C_2$–$C_3$-alkylene and other substituents, for instance as described in the examples; or 1- or 2-naphthyl; or 1- or 2-phenanthrenyl. Lower alkylenedioxy is a divalent substituent attached to two adjacent carbon atoms of phenyl, e.g. methylenedioxy or ethylenedioxy. Oxy-$C_2$–$C_3$-alkylene is also a divalent substituent attached to two adjacent carbon atoms of phenyl, e.g. oxyethylene or oxypropylene. An example for oxy-$C_2$–$C_3$-alkylene-phenyl is 2,3-dihydrobenzofuran-5-yl.

Preferred as carbocyclic aryl is naphthyl, phenyl or phenyl optionally substituted, for instance, as described in the examples, e.g. mono- or disubstituted by lower alkoxy, phenyl, halogen, lower alkyl or trifluoromethyl.

Heterocyclic aryl represents monocyclic or bicyclic heteroaryl, for example pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted as defined above.

Preferably, heterocyclic aryl is pyridyl, indolyl, quinolinyl, pyrrolyl, thiazolyl, isoxazolyl, triazolyl, tetrazolyl, pyrazolyl, imidazolyl, thienyl, or any said radical substituted, especially mono- or di-substituted as defined above.

Cycloalkyl represents a saturated cyclic hydrocarbon optionally substituted by lower alkyl which contains 3 to 10 ring carbons and is advantageously cyclopropyl, cyclopentyl, cyclohexyl, cycloheptyl or cyclooctyl optionally substituted by lower alkyl.

N-heterocyclyl is as defined above. Preferred N-heterocyclic substituents are optionally substituted pyrrolidine, pyrrole, diazole, triazole, tetrazole, imidazole, oxazole, thiazole, pyridine, pyrimidine, triazine, piperidine, piperazine, morpholine, phthalimde, hydantoin, oxazolidinone or 2,6-dioxo-piperazine and, for example, as hereinafter described in the examples.

In a further embodiment the invention provides a compound of formula IIa, or a pharmaceutically acceptable salt or ester thereof

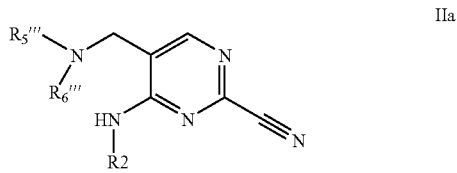

IIa wherein R2 is as defined above and R5''' and R6''' are as defined above for R5 and R6 respectively.

R2 is preferably R2' which is lower alkyl, e.g. straight chain or more preferably branched-chain $C_1$–$C_6$ alkyl, e.g. especially 2-ethylbutyl, isobutyl, or 2,2-dimethylpropyl; or $C_3$–$C_6$ cycloalkyl, especially cyclopropyl, cyclopentyl or cyclohexyl.

R5''' and R6''' may be such that R5''' and R6''' together with the nitrogen atom to which they are joined to form an N-heterocyclyl group R5''' is preferably optionally substituted (aryl-lower-alkyl, heterocyclyl-aryl, N-heterocyclyl-aryl or aryl-N-heterocyclyl (where N-heterocyclyl is as defined above).

R5''' is preferably optionally substituted by from 1–4 substituents selected from halo, hydroxy, nitro, cyano, lower-alkyl, lower-alkoxy or lower-alkoxy-lower-akyl.

For example, R5''' is 4-methoxy-benzyl, 3-methoxy-benzyl, 4-(4-methyl-piperazin-1-yl)-benzyl, 4-[4-(2-ethoxy-ethyl)-piperazin-1-yl]-benzyl, 1-methyl-1-phenyl-ethyl, 2-(4-methoxy-phenyl)-1,1-dimethyl-ethyl, 2-(4-fluoro-phenyl)-1,1-dimethyl-ethyl, 4-(4-methyl-piperazin-1-yl)-phenyl]-ethyl, 2-[4-(4-isopropyl-piperazin-1-yl)-phenyl]-1,1-dimethyl-ethyl, 2-{4-[4-(2-methoxy-ethyl)-piperazin-1-yl]-phenyl}-1,1-dimethyl-ethyl, 2-{3-[4-(2-ethoxy-ethyl)-piperazin-1-yl]-phenyl}-1,1-dimethyl-ethyl, 2-[3-(4-ethyl-piperazin-1-yl)-phenyl]-1,1-dimethyl-ethyl, 2-[3-(4-isopropyl-piperazin-1-yl)-phenyl]-1,1-dimethyl-ethyl, 1,1-dimethyl-2-(3-pyrrolidin-1-yl-phenyl)-ethyl, 2-{3-[4-(2-methoxy-ethyl)-piperazin-1-yl]-phenyl}-1,1-dimethyl-ethyl, 2-(4-methoxy-phenyl)-ethyl 2-[4-(4-methyl-piperazin-1-yl)-phenyl]-ethyl, 2-[4-(4-isopropyl-piperazin-1-yl)-phenyl]-ethyl, 2-{4-[4-(2-methoxy-ethyl)-piperazin-1-yl]-phenyl}-ethyl, 2-(3-methoxy-phenyl)-ethyl, 2-[3-(4-methyl-piperazin-1-yl)-phenyl]-ethyl, 2-[4-(4-isopropyl-piperazin-1-yl)-phenyl]-ethyl, 2-pyrrol-1-yl-ethyl, 3-piperidin-1-yl-propyl 2-(4-methoxy-phenyl)-2-methyl-propyl, 2-methyl-2-[4-(4-methyl-piperazin-1-yl)-phenyl]-propyl, 2-[4-(4-isopropyl-piperazin-1-yl)-phenyl]-2-methyl-propyl, 2-{4-[4-(2-ethoxy-ethyl)-piperazin-1-yl]-phenyl}-2-methyl-propyl, 2-{4-[pyrimidin-1-yl]-phenyl}-2-methyl-propyl, 4-(3-methoxy-phenyl)-piperazin-1-yl-methyl, 4-(4-methoxy-phenyl)-piperazin-1-yl-methyl, 1-methyl-1-(1-phenyl-cyclopropyl)-ethyl, For example, R5''' and R6''' together with the nitrogen atom to which they are joined to form an N-heterocyclyl group is 4-(2-pyridin-4-yl-ethyl)-piperazin-1-yl, [4-(2-pyridin-2-yl-ethyl)-piperazin-1-yl, 4-pyridin-4-ylmethyl-piperazin-1-yl, 4-(2-piperidin-1-yl-ethyl)-piperazin-1-yl, 4-(2-pyrrolidin-1-yl-ethyl)-piperazin-1-yl, 4-(2-Diethylamino-ethyl)-piperazin-1-yl, 4-(3-Diethylamino-propyl)-piperazin-1-yl, 4-(1-methyl-piperidin-4-yl)-piperazin-1-yl, 4-pyrrolidin-1-yl-piperidin-1-yl, 4-(2-methoxy-ethyl)-piperazin-1-yl In a preferred embodiment the invention provides a compound of formula II, or a pharmaceutically acceptable salt or ester thereof

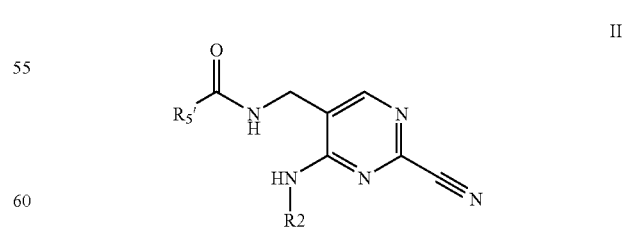

II wherein R2 is as defined above and R5' is as defined above for R5.

R2 is preferably R2' which is lower alkyl, e.g. straight chain or more preferably branched-chain $C_1$–$C_6$ alkyl, e.g.

especially 2-ethylbutyl, isobutyl, or 2,2-dimethylpropyl; or $C_3$–$C_6$cycloalkyl, especially cyclopropyl, cyclopentyl or cyclohexyl.

R5' is preferably optionally substituted (aryl-lower-alkyl, heterocyclyl-aryl, N-heterocyclyl-aryl or aryl-N-heterocyclyl (where N-heterocyclyl is as defined above).

R5' is preferably optionally substituted by from 1–4 substituents selected from halo, hydroxy, nitro, cyano, lower-alkyl, lower-alkoxy, lower-alkoxy-carbonyl or lower-alkoxy-lower-akyl.

For example, R5' is 4-methoxy-phenyl, 4-(1-propyl-piperidin-4-yl)-phenyl, 4-(4-methyl-piperazin-1-yl)-phenyl, 4-[1-(2-methoxy-ethyl)-piperidin-4-yl]-phenyl, 4-(4-propyl-piperazin-1-yl)-phenyl, 3-[4-(4-methyl-piperazin-1-yl)-phenyl]-propionyl, 3-[3-(4-methyl-piperazin-1-yl)-phenyl]-propionyl, 4-(4-ethyl-piperazin-1-yl)-phenyl, 4-(4-isopropyl-piperazin-1-yl)-phenyl, 4-[4-(2-ethoxy-ethyl)-piperazin-1-yl]-phenyl, 4-[4-(2-methoxy-ethyl)-piperazin-1-yl]-phenyl, 4-piperazin-1-yl-phenyl, 4-[4-(carboxylic acid tert-butyl ester) piperazino-1-yl-]-phenyl, 3-[4-(carboxylic acid tert-butyl ester) piperazino-1-yl-]-phenyl, 3-(4-methyl-piperazin-1-yl)-phenyl, 3-(4-ethyl-piperazin-1-yl)-phenyl, 3-(4-isopropyl-piperazin-1-yl)-phenyl, 3-[4-(2-methoxy-ethyl)-piperazin-1-yl]-phenyl, 3-[4-(2-ethoxy-ethyl)-piperazin-1-yl]-phenyl, 3-(2-pyrrolidin-1-yl-ethoxy)-phenyl, 3-(2-dimethylamino-ethoxy)-4-methoxy-phenyl, 4-dimethylaminomethyl-phenyl, 4-(4-methyl-piperazin-1-ylmethyl)-phenyl, 4-[1-(2-methoxy-ethyl)-piperidin-4-ylmethyl]-phenyl, 4-methoxy-3-(2-piperidin-1-yl-ethoxy)-phenyl, 3-[4-(4-ethyl-piperazin-1-yl)-phenyl]-2,2-dimethyl-propionyl, 3-[4-(4-propyl-piperazin-1-yl)-phenyl]-propionyl, 3-(4-pyrrolidin-1-yl-phenyl)-propionyl, 3-[3-(4-ethyl-piperazin-1-yl)-phenyl]-2,2-dimethyl-propionyl, 3-{3-[4-(2-methoxy-ethyl)-piperazin-1-yl]-phenyl}-2,2-dimethyl-propionyl, 3-{3-[4-(2-ethoxy-ethyl)-piperazin-1-yl]-phenyl}-2,2-dimethyl-propionyl, 3-(3-pyrrolidin-1-yl-phenyl)-propionyl, 2-[4-(4-methyl-piperazin-1-yl)-phenyl]-isobutyl, 2-(4-methoxy-phenyl)-acetyl, 2-(3-methoxy-phenyl)-acetyl, 2-[4-(4-methyl-piperazin-1-yl)-phenyl]-acetyl, 2-[4-(4-ethyl-piperazin-1-yl)-phenyl]-acetyl, 2-[4-(4-isopropyl-piperazin-1-yl)-phenyl]-acetyl, 2-(4-pyrrolidin-1-yl-phenyl)-acetyl, 2-[4 (2-diethylamino-ethylamino)-phenyl]-isobutyl, 2-(4-pyrrolidin-1-yl-phenyl)-isobutyl.

In a further preferred embodiment the invention provides a compound of formula III or a pharmaceutically acceptable salt or ester thereof

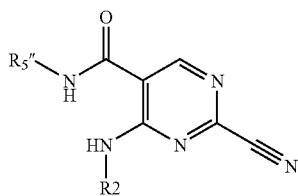

III wherein R2 is as defined above and R5" is as defined above for R5.

R2 is preferably R2" which is lower alkyl, e.g. straight chain or more preferably branched-chain $C_1$–$C_6$ alkyl, e.g. especially 2-ethylbutyl, isobutyl, or 2,2-dimethylpropyl; or $C_3$–$C_6$cycloalkyl, especially cyclopropyl, cyclopentyl or cyclohexyl.

R5" is preferably optionally substituted (aryl-loweralkyl, aryl—aryl, N-heterocyclyl-aryl or aryl-N-heterocyclyl (where N-heterocyclyl is as defined above).

R5" is preferably optionally substituted by from 1–4 substituents selected from halo, hydroxy, nitro, cyano, optionally mono- or di-loweralkyl substituted amino, oxo, lower-alkyl, lower-alkenyl, lower-alkynyl, $C_3$–$C_{10}$cycloalkyl or $C_3$–$C_{10}$cycloalkyl-lower-alkyl.

For example, R5" is 4-methoxybenzyl, 5-methyl-2-phenyl-2.H.-pyrazol-3-yl, 4-chlorobenzyl, 4-dimethylaminobenzyl, benzyl, 2-phenyl-2.H.-pyrazol-3-yl, 2-phenyl-phenyl, 2-pyrrol-1-yl-phenyl, 2-imidazol-1-yl-phenyl, 5-methyl-2-(4-chlorophenyl)-2.H.-pyrazol-3-yl, 5-methyl-2-(2-chlorophenyl)-2.H.-pyrazol-3-yl and 5-methyl-2-(2,4-dichlorophenyl)-2.H.-pyrazol-3-yl, 2-(4-methoxy-phenyl)-1,1-dimethyl-ethyl, 1,1-dimethyl-2-[3-(4-methyl-piperazin-1-yl)-phenyl]-ethyl, 1,1-dimethyl-2-[4-(4-methyl-piperazin-1-yl)-phenyl]-ethyl, 1,1-dimethyl-2-[3-(2-pyrrolidin-1-yl-ethylamino)-phenyl]-ethyl, 2-{3-[4-(2-ethoxy-ethyl)-piperazin-1-yl]-phenyl}-1,1-dimethyl-ethyl, 2-(4-difluoromethoxy-phenyl)-ethyl, 2-[3-(4-methyl-piperazin-1-yl)-phenyl]-ethyl.

Particularly preferred compounds of the invention are the compounds of formula II, IIa and III as described in the examples.

Compounds of formula II, or pharmaceutically acceptable salts or ester thereofs

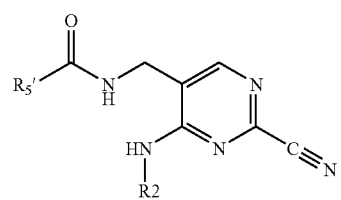

II wherein R2 and R5' are as defined above, may be prepared by cyanation of a 2-chloro precursor of formula IV

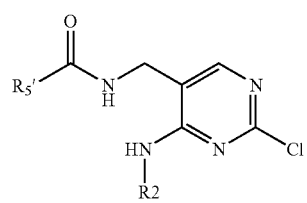

IV wherein R2 and R5' are as defined above; for instance, substantially as described in the examples.

The above cyanation reactions may be carried out under various conditions and in the presence of solvents and other reagents as required, including catalysts and co-factors as known in the art and for instance, as hereinafter described in the examples.

The starting materials may be prepared and the coupled and cyclised products may be converted into other compounds of formula II and salts and esters thereof using methods and procedures known in the art, and as hereinafter described in the examples.

Accordingly the present invention further provides a process for the preparation of a compound of Formula II or a pharmaceutically acceptable salt or ester thereof

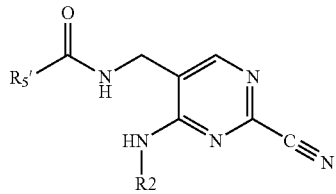

II wherein R2 and R5' are as defined above, comprising cyanation of a 2-chloro precursor of formula IV

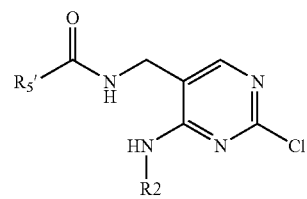

IV wherein R2 and R5' are as defined above, and thereafter, if desired, converting the product obtained into a further compound of formula II, or into a salt or ester thereof.

Compounds of Formula IIa or a pharmaceutically acceptable salt or ester thereof

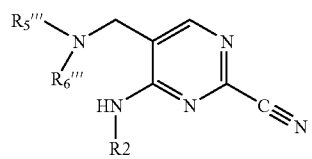

IIa wherein R2, R5" and R6''' are as defined above, comprising cyanation of a 2-chloro precursor of formula IVa

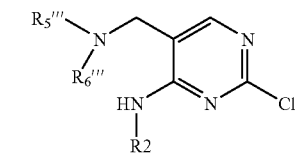

IVa wherein R2, R5" and R6''' are as defined above, and thereafter, if desired, converting the product obtained into a further compound of formula IIa, or into a salt or ester thereof.

Compounds of formula III or pharmaceutically acceptable salts or esters thereof

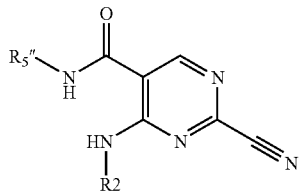

III wherein R2 and R5" are as defined above, may be prepared either by cyanation of a 2-chloro precursor of formula V

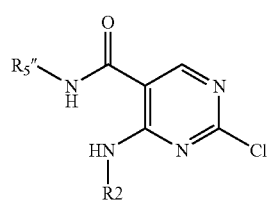

V or coupling of a carboxylic acid precursor of formula VI with a corresponding amine of formula VII

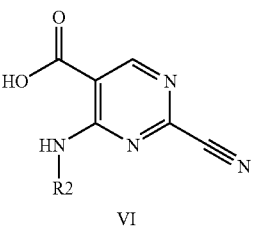

VI wherein the R2 and R5" are as defined above; for instance, substantially as described in the examples.

The above coupling and cyanation reactions may be carried out under various conditions and in the presence of solvents and other reagents as required, including catalysts and co-factors as known in the art and for instance, as hereinafter described in the examples.

The starting materials may be prepared and the coupled and cyclised products may be converted into other compounds of formula III and salts and esters thereof using methods and procedures known in the art, and as hereinafter described in the examples.

Accordingly the present invention further provides a process for the preparation of a compound of Formula III or a pharmaceutically acceptable salt or ester thereof

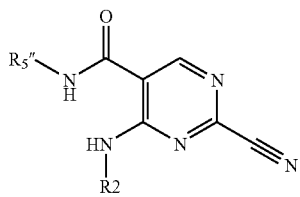

wherein R2 and R3 are as defined above, comprising either cyanation of a 2-chloro precursor of formula V

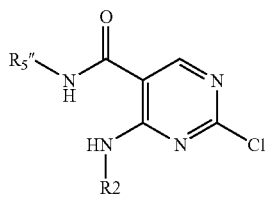

or coupling of a carboxylic acid precursor of formula VI with a corresponding amine of formula VII

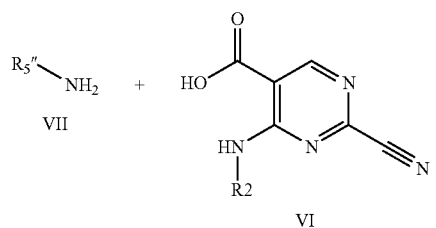

wherein the R2 and R5″ are as defined above, and thereafter, if desired, converting the product obtained into a further compound of formula III, or into a salt or ester thereof.

Compounda of formula I, II and III as defined above and the compounds of the Examples are hereinafter referred to as Compounds of the Invention.

Compounds of the invention are either obtained in the free form, or as a salt thereof if salt forming groups are present.

Compounds of the Invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The compounds of the invention exhibit valuable pharmacological properties in mammals and are particularly useful as inhibitors of cathepsin K.

The cathepsin K inhibitory effects of the compound of the invention can be demonstrated in vitro by measuring the inhibition of e.g. recombinant human cathepsin K.

The in vitro assay is carried out as follows:

For cathepsin K:

The assay is performed in 96 well microtiter plates at ambient temperature using recombinant human cathepsin K. Inhibition of cathepsin K is assayed at a constant enzyme (0.16 nM) and substrate concentration (54 mM Z-Phe-Arg-AMCA-Peptide Institute Inc. Osaka, Japan) in 100 mM sodium phosphate buffer, pH 7.0, containing 2 mM dithiothreitol, 20 mM Tween 80 and 1 mM EDTA. Cathepsin K is preincubated with the inhibitors for 30 min, and the reaction is initiated by the addition of substrate. After 30 min incubation the reaction is stopped by the addition of E-64 (2 mM), and fluorescence intensity is read on a multi-well plate reader at excitation and emission wavelengths of 360 and 460 nm, respectively. Compounds of the Invention typically have $IC_{50}$s for inhibition of human cathepsin K of less than about 100 nM down to about 1 nM or less, preferably of about 5 nM or less, e.g. about 1 nM. Thus for example, the compounds of Examples I-22 and I-23 have $IC_{50}$s for inhibition of human cathepsin K of 3 nM and 1.5 nM respectively.

In view of their activity as inhibitors of cathepsin K, Compounds of the Invention are particularly useful in mammals as agents for treatment and prophylaxis of diseases and medical conditions involving elevated levels of cathepsin K. Such diseases include diseases involving infection by organisms such as *pneumocystis carinii, trypsanoma cruzi, trypsanoma brucei, crithidia fusiculata*, as well as parasitic diseases such as schistosomiasis and malaria, tumours (tumour invasion and tumour metastasis), and other diseases such as metachromatic leukodystrophy, muscular dystrophy, amytrophy and similar diseases.

Cathepsin K, has been implicated in diseases of excessive bone loss, and thus the Compounds of the Invention may be used for treatment and prophylaxis of such diseases, including osteoporosis, gingival diseases such as gingivitis and periodontitis, Paget's disease, hypercalcemia of malignancy, e.g. tumour-induced hypercalcemia and metabolic bone disease. Also the Compounds of the Invention may be use for treatment or prophylaxis of diseases of excessive cartilage or matrix degradation, including osteoarthritis and rheumatoid arthritis as well as certain neoplastic diseases involving expression of high levels of proteolytic enzymes and matrix degradation.

Compounds of the Invention, are also indicated for preventing or treating coronary disease, atherosclerosis (including atherosclerotic plaque rupture and destabilization), autoimmune diseases, respiratory diseases and immunologically mediated diseases (including transplant rejection).

Compounds of the Invention are particularly indicated for preventing or treating osteoporosis of various genesis (e.g. juvenile, menopausal, post-menopausal, post-traumatic, caused by old age or by cortico-steroid therapy or inactivity).

Beneficial effects are evaluated in in vitro and in vivo pharmacological tests generally known in the art, and as illustrated herein.

The above cited properties are demonstrable in in vitro and in vivo tests, using advantageously mammals, e.g. rats, mice, dogs, rabbits, monkeys or isolated organs and tissues, as well as mammalian enzyme preparations, either natural or prepared by e.g. recombinant technology. Compounds of the Invention can be applied in vitro in the form of solutions, e.g. preferably aqueous solutions or suspensions, and in vivo either enterally or parenterally, advantageously orally, e.g. as a suspension or in aqueous solution, or as a solid capsule or tablet formulation. The dosage in vitro may range between about $10^{-5}$ molar and $10^{-9}$ molar concentrations. The dosage in vivo may range, depending on the route of administration, between about 0.1 and 100 mg/kg.

The antiarthritic efficacy of the Compounds of the Invention for the treatment of rheumatoid arthritis can be determined using models such as or similar to the rat model of adjuvant arthritis, as described previously (R. E. Esser, et. al. J. Rheumatology, 1993, 20, 1176.)

The efficacy of the compounds of the invention for the treatment of osteoarthritis can be determined using models such as or similar to the rabbit partial lateral meniscectomy model, as described previously (Colombo et al. Arth. Rheum. 1993 26, 875–886). The efficacy of the compounds in the model can be quantified using histological scoring methods, as described previously (O'Byrne et al. Inflamm Res 1995, 44, S117–S118).

The efficacy of the compounds of the invention for the treatment of osteoporosis can be determined using an animal model such as the ovariectomised rat or other similar species, e.g. rabbit or monkey, in which test compounds are administered to the animal and the presence of markers of bone resorption are measured in urine or serum (e.g. as described in Osteoporos Int (1997) 7:539–543).

Accordingly in further aspects the invention provides:

A Compound of the Invention for use as a pharmaceutical;

a pharmaceutical composition comprising a Compound of the Invention as an active ingredient;

a method of treating a patient suffering from or susceptible to a disease or medical condition in which cathepsin K is implicated, comprising administering an effective amount of a Compound of the Invention to the patient, and the use of a Compound of the Invention for the preparation of a medicament for therapeutic or prophylactic treatment of a disease or medical condition in which cathepsin K is implicated.

The present invention relates to methods of using Compounds of the Invention and their pharmaceutically acceptable salts, or pharmaceutical compositions thereof, in mammals for inhibiting cathepsin K, and for the treatment of cathepsin K dependent conditions, such as the cathepsin K dependent conditions, described herein, e.g. inflammation, osteoporosis, rheumatoid arthritis and osteoarthritis.

Particularly the present invention relates to a method of selectively inhibiting cathepsin K activity in a mammal which comprises administering to a mammal in need thereof an effective cathepsin K inhibiting amount of a Compound of the Invention.

More specifically such relates to a method of treating osteoporosis, rheumatoid arthritis, osteoarthritis, and inflammation (and other diseases as identified above) in mammals comprises administering to a mammal in need thereof a correspondingly effective amount of a Compound of the Invention.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art.

EXAMPLES

Example I describes the preparation of 2-Cyano-Pyrimidine-5-ylmethyl-amides

1. N-[2-Cyano-4-(2,2-dimethyl-propylamino)-Pyrimidin-5-ylmethyl]-2-(4-methoxy-phenyl)-acetamide

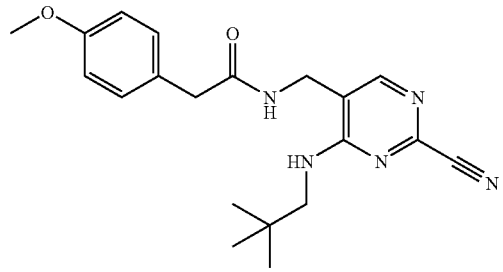

A. 2,4-Dichloro-5-choromethyl-pyrimidine

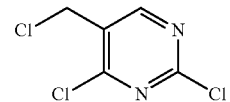

To 50 ml of $POCl_3$ is added 21.5 g (103.5 mmol) of $PCl_5$ and 4.0 g (27.6 mmol) of 5-(hydroxymethyl)-uracil. The resulting reaction mixture is stirred at 115° C. for 15 h. The reaction mixture is then cooled to r.t. and distilled, to yield 2,4-dichloro-5-choromethyl-pyrimidine as a colourless liquid, boiling point 74° C. (0.01 mbar).

$^1$H-NMR (300 MHz, $CDCl_3$): 8.64 (s, 1H), 4.62 (s, 2H).

B. (2-Chloro-5-chloromethyl-pyrimidin-4-yl)-(2,2-dimethyl-propyl)-amine

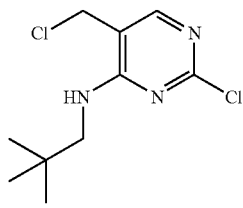

A solution of 3.47 g (17.57 mmol) of 2,4-dichloro-5-choromethyl-pyrimidine and 2.9 ml (21.08 mmol) triethylamine in 29 ml of THF is cooled to −5° C. and 2.2 ml (17.57 mmol) 2,2-dimethyl-propylamin is added over a period of 15 minutes. The reaction mixture is stirred at −5° C. for additional 2 h, then diluted with ethyl acetate and extracted once with brine. The organic layer is separated and dried over Na$_2$SO$_4$. Purification of the crude product by flash chromatography (hexanes/ethyl acetate) yields (2-chloro-5-chloromethyl-pyrimidin-4-yl)-(2,2-dimethyl-propyl)-amine as white crystals.

MS (ES+): 249 (M+H)$^+$
$^1$H-NMR (300 MHz, CDCl$_3$): 7.94 (s, 1H), 5.4 (m (broad), 1H), 4.47 (s, 2H), 3.4 (d, 2H), 1.02 (s, 9H).

C. (5-Azidomethyl-2-chloro-pyrimidin-4-yl)-(2,2-dimethyl-propyl)-amine

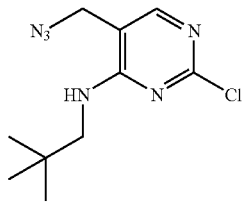

A solution of 1.47 g (5.92 mmol) of (2-chloro-5-chloromethyl-pyrimidin-4-yl)-(2,2-dimethyl-propyl)-amine and 0.46 g (7.1 mmol) NaN$_3$ is dissolved in 6 ml of DMF and was stirred at 30° C. for 2.5 hours. Then the reaction mixture is cooled to rt., diluted with ethyl acetate and twice extracted with H$_2$O. The organic layer is separated and dried over Na$_2$SO$_4$. Evaporation of the ethyl acetate yielded (5-azidomethyl-2-chloro-pyrimidin-4-yl)-(2,2-dimethyl-propyl)-amine as white crystals.

Mp.: 133–136° C.
MS (ES+): 255 (M+H)$^+$
$^1$H-NMR (300 MHz, CDCl$_3$): 7.92 (s, 1H), 5.49 (t (broad), 1H), 4.2 (s, 2H), 3.37 (d, 2H), 1 (s, 9H).

D. (5-Aminomethyl-2-chloro-pyrimidin-4-yl)-(2,2-dimethyl-propyl)-amine

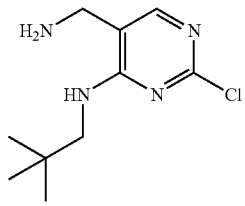

A solution of 1.47 g (15.77 mmol) (5-azidomethyl-2-chloro-pyrimidin-4-yl)-(2,2-dimethyl-propyl)-amine and 1.67 g (6.35 mmol) of triphenylphosphine in 20 ml of THF and 0.08 ml of H$_2$O is stirred at r.t. for 24 h. Then the solvent is removed and the residue dissolved in 40 ml EtOH and 17 ml NH$_3$ (25%). This reaction mixture is stirred for 48 h at r.t. and again the solvent is removed. The residue is dissolved in diethylether and twice extracted with 25 ml of 1N HCl. Both acidic extracts were combined and once more extracted with diethylether, then the acidic layer is evaporated under vacuo. The solid residue was triturated with diethylether yielding (5-Aminomethyl-2-chloro-pyrimidin-4-yl)-(2,2-dimethyl-propyl)-amine 2HCl as slightly yellow crystals.

MS (ES+): 229 (M+H)$^+$
$^1$H-NMR (300 MHz, CD$_3$OD): 8.27 (s, 1H), 4.19 (s, 2H), 3.57 (s, 2H), 1.01 (s, 9H).

E. N-[2-Chloro-4-(2,2-dimethyl-propylamino)-pyrimidin-5-ylmethyl]-2-(4-methoxy-phenyl)acetamide

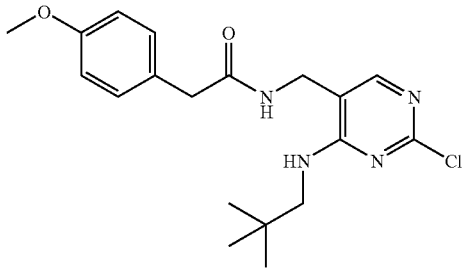

To a solution of 0.089 g (0.38 mmol) of (5-aminomethyl-2-chloro-pyrimidin-4-yl](2,2-dimethyl-propyl)-amine and 0.27 ml (1.6 mmol) DIEA in 2.5 ml of DMF 0.063 g (0.38 mmol) of (4-methoxy-phenyl)-acetic acid is added and the reaction mixture is stirred at r.t for 16 h. The reaction mixture is then diluted with ethyl acetate and twice washed with H$_2$O, the organic layer is separated and dried over Na$_2$SO$_4$ and then concentrated under reduced pressure. Flash chromatography (ethyl acetate/hexanes 1:1) of the residue provided N-[2-chloro-4-(2,2-dimethyl-propylamino)-pyrimidin-5-ylmethyl]-2-(4-methoxy-phenyl)acetamide as white crystals.

MS (ES+): 377 (M+H)$^+$
$^1$H-NMR (300 MHz, CDCl$_3$): 7.55 (s, 1H), 7.11 (m, 3H), 6.85 (d, 2H), 6.22 (t, 1H), 4.2 (d, 2H), 3.79 (s, 3H), 3.53 (s, 2H), 3.3 (d, 2H), 0.98 (s, 9H).

F. N-[2-Cyano-4-(2,2-dimethyl-propylamino)-pyrimidin-5-ylmethyl]-2-(4-methoxy-phenyl)-acetamide

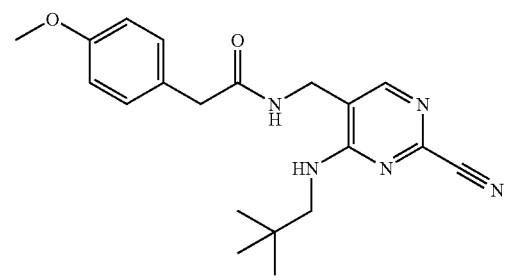

A solution of 0.036 g (0.096 mmol) of N-[2-chloro-4-(2,2-dimethyl-propylamino)-pyrimidin-5-ylmethyl]-2-(4-methoxy-phenyl)acetamide, 0.013 g (0.192 mmol) of KCN and 0.011 g (0.096 mmol) of 1.4-diazabicyclo[2.2.2]octan in 1 ml of DMSO/H$_2$O (85:15) is stirred for 45 minutes at 60° C. The reaction mixture is cooled to r.t. and subjected to preparative HPLC. N-[2-cyano-4-(2,2-dimethyl-propylamino)-pyrimidin-5-ylmethyl]-2-(4-methoxy-phenyl)-acetamide is obtained as a white solid.

MS (ES+): 368 (M+H)$^+$
$^1$H-NMR (300 MHz, CDCl$_3$): 7.81 (s, 1H), 7.28 (t, 2H), 7.13 (d, 2H), 6.88 (d, 2H), 5.85 (t, 1H), 4.25 (d, 2H), 3.8 (s, 3H), 3.54 (s, 2H, 3.32 (d, 2H), 1.0 (s, 9H).

By repeating the procedure described above in example 1, using the appropraite starting materials and conditions the following compounds of formula 2–7 are obtained as identified below in table.

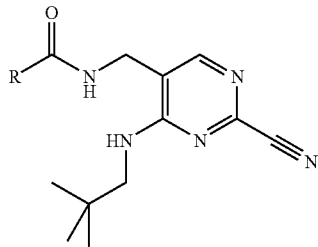

| Ex. | R | MS (ES+) (M + H)+ | 1H-NMR |
|---|---|---|---|
| I-1 N-[2-Cyano-4-(2,2-dimethyl-propylamino)-pyrimidin-5-ylmethyl]-4-(1-propyl-piperidin-4-yl)-benzamide | (structure: 4-(1-propyl-piperidin-4-yl)phenyl) | 449 | (300MHz, CDCl3): 7.95(s, 1H), 7.72(d, 2H), 7.5(t, 1H), 7.32(d, 2H), 6.8(t, 1H), 4.51(d, 2H), 3.32(d, 2H), 3.08(d, 2H), 2.58(m, 1H), 2.39(m, 2H), 2.08(m, 2H), 1.82 (m, 4H), 1.59(q, 2H), 0.98 (s, 9H), 0.91(t, 3H). |
| I-2 N-[2-Cyano-4-(2,2-dimethyl-propylamino)-pyrimidin-5-ylmethyl]-4-(4-methyl-piperazin-1-yl)-benzamide | (structure: 4-(4-methyl-piperazin-1-yl)phenyl) | 422 | (300MHz, CDCl3): 7.9(s, 1H), 7.69(d, 2H), 7.6(t, 1H), 6.89(d, 2H), 6.68(t, 1H), 4.5(d, 2H), 3.33(m, 6H), 2.59(m, 4H), 2.38(s, 3H), 0.99(s, 9H). |
| I-3 N-[2-Cyano-4-(2,2-dimethyl-propylamino)-pyrimidin-5-ylmethyl]-4-[1-(2-methoxy-ethyl)-piperidin-4-yl]-benzamide | (structure: 4-[1-(2-methoxy-ethyl)-piperidin-4-yl]phenyl) | 465 | (300MHz, CDCl3): 7.94(s, 1H), 7.72(d, 2H), 7.5(t, 1H), 7.29(d, 2H), 6.8(t, 1H), 4.52(d, 2H), 3.55(t, 2H), 3.38(s, 3H), 3.36(d, 2H), 3.13(m, 2H), 2.65(t, 2H), 2.6(t, 3H), 2.17(m, 2H), 1.82(m, 4H), 0.99(s, 9H). |
| I-4 N-[2-Cyano-4-(2,2-dimethyl-propylamino)-pyrimidin-5-ylmethyl]-4-(4-propyl-piperazin-1-yl)-benzamide | (structure: 4-(4-propyl-piperazin-1-yl)phenyl) | 450 | (300MHz, CDCl3): 7.9(s, 1H), 7.69(d, 2H), 7.6(t, 1H), 6.87(d, 2H), 6.59(t, 1H), 4.5(d, 2H), 3.34(m, 6H), 2.6(m, 4H), 2.35(t, 2H), 2.45(m, 2H), 0.99(s, 9H), 0.98(t, 3H). |
| I-5 N-[2-Cyano-4-(2,2-dimethyl-propylamino)-pyrimidin-5-ylmethyl]-2,2-dimethyl-3-[4-(4-methyl-piperazin-1-yl)-phenyl]-propionamide | (structure: 4-(4-methyl-piperazin-1-yl)phenyl propionamide) | 478 | (300MHz, CDCl3): 7.72(s, 1H), 7.62(t, 1H), 6.88(d, 2H), 6.69(d, 2H), 5.8(m, 1H), 4.19(d, 2H), 3.38(d, 2H), 3.18(m, 4H), 2.71(s, 2H), 2.65(m, 4H), 2.39(s, 3H), 1.1(s, 6H), 1.01(s, 9H). |
| I-6 N-[2-Cyano-4-(2,2-dimethyl-propylamino)-pyrimidin-5-ylmethyl]-2,2-dimethyl-3-[3-(4-methyl-piperazin-1-yl)-phenyl]-propionamide | (structure: 3-(4-methyl-piperazin-1-yl)phenyl propionamide) | 478 | (300MHz, CDCl3): 7.8(s, 1H), 7.51(t, 1H), 7.04(t, 1H), 6.69(d, 1H), 6.61(s, 1H), 6.52(d, 1H), 5.85(m, 1H), 4.19(d, 2H), 3.35(d, 2H), 3.19(m, 4H), 2.79(s, 2H), 2.63(m, 4H), 2.4(s, 3H), 1.1(s, 6H), 1.01(s, 9H). |

-continued

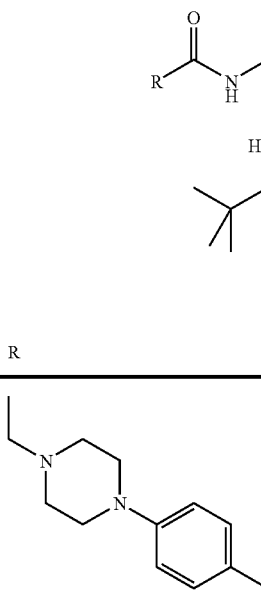

| Ex. | R | MS (ES+) (M + H)+ | 1H-NMR |
|---|---|---|---|
| I-7 N-[2-Cyano-4-(2,2-dimethyl-propylamino)-pyrimidin-5-ylmethyl]-4-(4-ethyl-piperazin-1-yl)-benzamide | 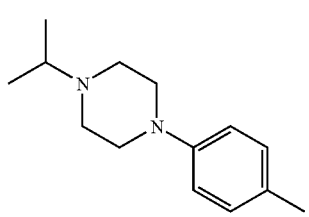 | 436 | (300MHz, CDCl3): 7.92(s, 1H), 7.68(d, 2H), 7.58(t, 1H), 6.86(d, 2H), 6.56(t, 1H), 4.49(d, 2H), 3.32(m, 6H), 2.60(mm, 6H) 2.4(q, 2H) 1.12(t, 3H), 0.98(s, 9H). |
| I-8 N-[2-Cyano-4-(2,2-dimethyl-propylamino)-pyrimidin-5-ylmethyl]-4-(4-isopropyl-piperazin-1-yl)-benzamide | 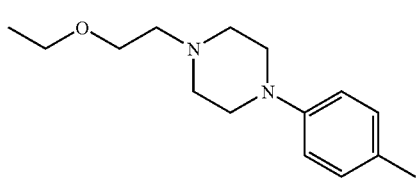 | 450 | (300MHz, CDCl3): 7.92(s, 1H), 7.65(d, 2H), 7.54(t, 1H), 6.88(d, 2H), 6.46(t, 1H), 4.51(d, 2H), 3.32(m, 6H), 2.74(m, 1H), 2.68(m, 4H), 1.10(d, 6H), 0.98(s, 9H). |
| I-9 N-[2-Cyano-4-(2,2-dimethyl-propylamino)-pyrimidin-5-ylmethyl]-4-[4-(2-ethoxy-ethyl)-piperazin-1-yl]-benzamide | 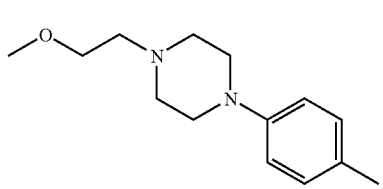 | 479 | (400MHz, CDCl3): 7.91(s, 1H), 7.59(d, 2H), 7.45(t, 1H), 6.79(d, 2H), 6.37(t, 1H), 4.45(d, 2H), 3.52(t, 2H), 3.47(q, 2h), 3.28(m, 6H), 2.58(m, 4H), 1.16(q, 3H), 0.98(s, 9H). |
| I-10 N-[2-Cyano-4-(2,2-dimethyl-propylamino)-pyrimidin-5-ylmethyl]-4-[4-(2-methoxy-ethyl)-piperazin-1-yl]-benzamide | 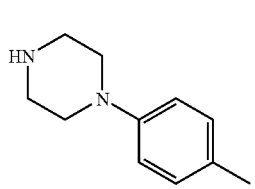 | 466 | (300MHz, CDCl3): 7.93(s, 1H), 7.68(d, 2H), 7.59(t, 1H), 6.87(d, 2H), 6.52(t, 1H), 4.50(d, 2H), 3.55(t, 2H), 3.38(s, 3H), 3.33(m, 6H), 2.63(m, 6H), 0.98(s, 9H). |
| I-11 N-[2-Cyano-4-(2,2-dimethyl-propylamino)-pyrimidin-5-ylmethyl]-4-piperazin-1-yl-benzamide | 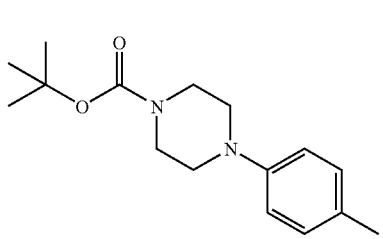 | 408 | (400MHz, CDCl3): 7.87(s, 1H), 7.61(d, 2H), 7.50(t, 1H), 6.80(d, 2H), 6.48(t, 1H), 4.44(d, 2H), 3.27(d, 2H), 3.20(m, 4H), 2.95(m, 4H), 0.90(s, 9H). |
| I-12 4-(4-{[2-Cyano-4-(2,2-dimethyl-propylamino)-pyrimidin-5-ylmethyl]-carbamoyl}-phenyl)-piperazine-1-carboxylic acid tert-butyl ester |  | 508 | (300MHz, CDCl3): 7.95(s, 1H), 7.68(d, 2H), 7.54(t, 1H), 6.88(d, 2H), 6.44(t, 1H), 4.52(d, 2H), 3.56(m, 4H), 3.36(d, 2H), 3.0(m, 4H), 1.48(s, 9H), 0.98(s, 9H). |

-continued

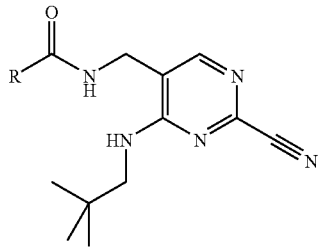

| Ex. | R | MS (ES+) (M + H)+ | 1H-NMR |
|---|---|---|---|
| I-13<br>4-(3-{[2-Cyano-4-(2,2-dimethyl-propylamino)-pyrimidin-5-ylmethyl]-carbamoyl}-phenyl)-piperazine-1-carboxylic acid tert-butyl ester | | 508 | (300MHz, CDCl3):<br>7.91(s, 1H), 7.48(t, 1H),<br>7.35–7.18(m, 3H), 7.10–<br>7.02(m, 2H), 4.50(d, 2H),<br>3.55(m, 4H), 3.33(d, 2H),<br>3.16(m, 4H), 1.48(s, 9H),<br>0.99(s, 9H). |
| I-14<br>N-[2-Cyano-4-(2,2-dimethyl-propylamino)-pyrimidin-5-ylmethyl]-3-(4-methyl-piperazin-1-yl)-benzamide | | 422 | (400MHz, CDCl3):<br>7.78(s, 1H), 7.49(s, 1H),<br>7.31–7.07(m, 3H), 6.72<br>(2t(broad), 2H), 4.45(d,<br>2H), 3.30(m, 6H), 2.65<br>(m, 4H), 2.42(s, 3H), 0.98<br>(s, 9H). |
| I-15<br>N-[2-Cyano-4-(2,2-dimethyl-propylamino)-pyrimidin-5-ylmethyl]-3-(4-ethyl-piperazin-1-yl)-benzamide | | 436 | (400MHz, CDCl3):<br>7.74(s, 1H), 7.49(s, 1H),<br>7.32–7.07(m, 3H), 6.72<br>(2t(broad), 2H), 4.42(d,<br>2H), 3.30(m, 6H), 2.65<br>(m, 4H), 2.52(q, 2H),<br>1.18(t, 3H), 0.97(s, 9H). |
| I-16<br>N-[2-Cyano-4-(2,2-dimethyl-propylamino)-pyrimidin-5-ylmethyl]-3-(4-isopropyl-piperazin-1-yl)-benzamide | | 450 | (300MHz, CDCl3):<br>7.91(s, 1H), 7.44(t, 1H,<br>J=5Hz), 7.34–7.24(m,<br>3H), 7.11(d, 1H, J=7<br>Hz), 7.05(d, 1H, J=7<br>Hz), 6.83(t, 1H, J=6Hz),<br>4.50(d, 2H, J=6Hz),<br>3.32(d, 2H, J=5Hz),<br>3.25(m, 4H), 2.72(m,<br>1H), 2.68(m, 4H), 7.09<br>(d, 6H, J=8Hz), 0.98(s, 9H). |
| I-17<br>N-[2-Cyano-4-(2,2-dimethyl-propylamino)-pyrimidin-5-ylmethyl]-3-[4-(2-methoxy-ethyl)-piperazin-1-yl]-benzamide | | 466 | (300MHz, CDCl3):<br>7.94(s, 1H), 7.42(t, 1H),<br>7.32–7.26(m, 2H), 7.12–<br>7.04(m, 2H), 6.67(t, 1H),<br>4.52(d, 2H), 3.55(t, 2H),<br>3.37(s, 3H), 3.35(d, 2H),<br>3.26(m, 4H), 2.68–2.61<br>(m, 6H), 0.98(s, 9H). |
| I-18<br>N-[2-Cyano-4-(2,2-dimethyl-propylamino)-pyrimidin-5-ylmethyl]-3-[4-(2-ethoxy-ethyl)-piperazin-1-yl]-benzamide | | 479 | (300MHz, CDCl3):<br>7.92(s, 1H), 7.45(t, 1H),<br>7.36–7.26(m, 2H), 7.14–<br>7.02(m, 2H), 6.75(t, 1H),<br>4.52(d, 2H), 3.62(t, 2H),<br>3.55(q, 2H), 3.34(d, 2H),<br>3.23(m, 4H), 2.68–2.60<br>(m, 6H), 1.22(t, 3H), 0.99<br>(s, 9H). |

-continued

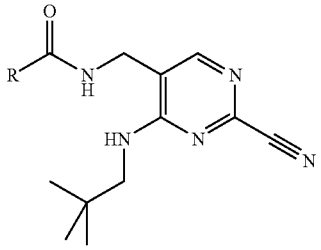

| Ex. | R | MS (ES+) (M + H)+ | 1H-NMR |
|---|---|---|---|
| I-19 N-[2-Cyano-4-(2,2-dimethyl-propylamino)-pyrimidin-5-ylmethyl]-4-methoxy-3-(2-pyrrolidin-1-yl-ethoxy)-benzamide | 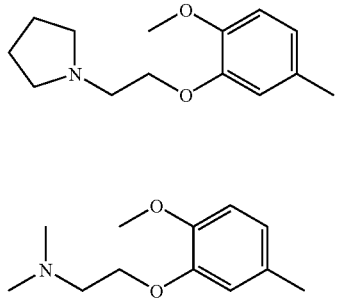 | 467 | (300MHz, CDCl$_3$): 7.89(s, 1H), 7.55(t, 1H), 7.44–7.35(m, 2H), 7.0 (t, 1H), 6.87(d, 1H), 4.50 (d, 2H), 4.20(t, 2H), 3.89 (s, 3H), 3.34(d, 2H), 2.94 (t, 2H), 2.62(m, 4H), 0.99 (s, 9H). |
| I-20 N-[2-Cyano-4-(2,2-dimethyl-propylamino)-pyrimidin-5-ylmethyl]-3-(2-dimethylamino-ethoxy)-4-methoxy-benzamide | 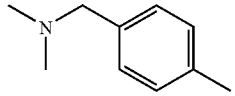 | 441 | (300MHz, CDCl$_3$): 7.92(s, 1H), 7.56(t, 1H), 7.42–7.35(m, 2H), 6.82 (d, 1H), 6.81(t, 1H), 4.52 (d, 2H), 4.18(t, 2H), 3.90 (s, 3H), 3.35(d, 2H), 2.80 (t, 2H), 2.37(s, 6H), 0.98 (s, 9H). |
| I-21 N-[2-Cyano-4-(2,2-dimethyl-propylamino)-pyrimidin-5-ylmethyl]-4-dimethylaminomethyl-benzamide | 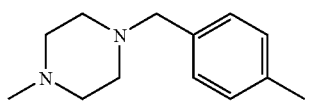 | 381 | (300MHz, CDCl$_3$): 7.91(s, 1H), 7.72(d, 2H, J=8Hz), 7.46(t, 1H, J=5 Hz), 7.39(d, 2H, J=8 Hz), 6.79(t, 1H, J=7Hz), 4.52(d, 2H, J=7Hz), 3.46(s, 2H), 3.35(d, 2H, J=5), 2.23(s, 6H), 0.99 (s, 9H). |
| I-22 N-[2-Cyano-4-(2,2-dimethyl-propylamino)-pyrimidin-5-ylmethyl]-4-(4-methyl-piperazin-1-ylmethyl)-benzamide | 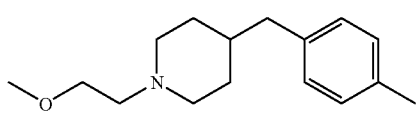 | 436 | (300MHz, CDCl$_3$): 7.91(s, 1H), 7.72(d, 2H, J= 8Hz), 7.44(t, 1H, J=5 Hz), 7.21(d, 2H, J=8 Hz), 6.87(t, 1H, J=7Hz), 4.52(d, 2H, J=7Hz), 3.54(s, 2H), 3.35(d, 2H, J=5Hz), 2.49(m, broad, 8H), 1.0(s, 9H). |
| I-23 N-[2-Cyano-4-(2,2-dimethyl-propylamino)-pyrimidin-5-ylmethyl]-4-[1-(2-methoxy-ethyl)-piperidin-4-ylmethyl]-benzamide | 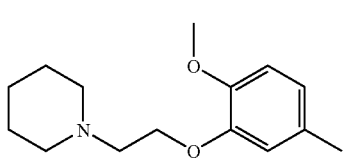 | 479 | (300MHz, CDCl$_3$): 7.89(s, 1H), 7.70(d, 2H), 7.53(t, 1H), 7.20(d, 2H), 6.88(t, 1H), 4.50(d, 2H), 3.48(t, 2H), 3.35(d, 2H), 3.33(s, 3H), 2.90(m, 2H), 2.60–2.50(, m, 4H), 1.90 (m, 2H), 1.60–1.28(M, 5H), 0.99(s, 9H). |
| I-24 N-[2-Cyano-4-(2,2-dimethyl-propylamino)-pyrimidin-5-ylmethyl]-4-methoxy-3-(2-piperidin-1-yl-ethoxy)-benzamide | | 481 | (300MHz, CDCl$_3$): 7.92(s, 1H), 7.56(t, 1H, J= 6Hz), 7.42–7.33(m, 2H), 6.88(d, 1H), 6.87(t, 1H), 4.50(d, 2H, J=7 Hz), 4.20(t, 2H, J=7Hz), 3.90(s, 3H), 3.36(d, 2H, J= 6Hz), 2.81((t, 2H, J=7 Hz), 2.51(m, 4H), 1.60 (m, 4H), 1.45(m, 2H), 0.98(s, 9H). |

-continued

| Ex. | R | MS (ES+) (M + H)+ | 1H-NMR |
|---|---|---|---|
| I-25 N-[2-Cyano-4-(2,2-dimethyl-propylamino)-pyrimidin-5-ylmethyl]-3-[4-(4-ethyl-piperazin-1-yl)-phenyl]-2,2-dimethyl-propionamide | | 492 | (300MHz, CDCl₃): 7.66(t, 1H), 7.62(s, 1H), 6.88(d, 2H), 6.67(d, 2H), 5.94(t, 1H), 4.18(d, 2H), 3.36(d, 2H), 3.14(m, 4H), 2.71(s, 2H), 2.60(m, 4H), 2.47(q, 2H), 1.19(s, 6H), 1.14(t, 3H), 1.02(s, 9H). |
| I-26 N-[2-Cyano-4-(2,2-dimethyl-propylamino)-pyrimidin-5-ylmethyl]-2,2-dimethyl-3-[4-(4-propyl-piperazin-1-yl)-phenyl]-propionamide | | 506 | (300MHz, CDCl₃): 7.68(s, 1H), 7.64(t, 1H), 6.89(d, 2H), 6.67(d, 2H), 5.89(t, 1H), 4.18(d, 2H), 3.36(d, 2H), 3.15(m, 4H), 2.72(s, 2H), 2.62(m, 4H), 2.37(m, 2H), 1.57(q, 2H), 1.20(s, 6H), 1.02(s, 9H). |
| I-27 N-[2-Cyano-4-(2,2-dimethyl-propylamino)-pyrimidin-5-ylmethyl]-2,2-dimethyl-3-(4-pyrrolidin-1-yl-phenyl)-propionamide | | 449 | (300MHz, CDCl₃): 7.69(s, 1H), 7.63(t, 1H), 6.84(d, 2H), 6.37(d, 2H), 5.84(t, 1H), 4.18(d, 2H), 3.37(d, 2H), 3.24(m, 4H), 2.69(s, 2H), 2.03(m, 4H), 1.18(s, 6H), 1.02(s, 9H). |
| I-28 N-[2-Cyano-4-(2,2-dimethyl-propylamino)-pyrimidin-5-ylmethyl]-3-[3-(4-ethyl-piperazin-1-yl)-phenyl]-2,2-dimethyl-propionamide | | 492 | (300MHz, CDCl₃): 7.78(s, 1H), 7.49(t, 1H), 7.04(t, 1H), 6.78(m, 1H), 6.62(m, 1H), 6.50(m, 1H), 5.82(t, 1H), 4.18(d, 2H), 3.34(d, 2H), 3.16(m, 4H), 2.79(s, 2H), 2.61(m, 4H), 2.48(q, 4H), 1.20(s, 6H), 1.13(t, 3H), 1.02(s, 9H). |
| I-29 N-[2-Cyano-4-(2,2-dimethyl-propylamino)-pyrimidin-5-ylmethyl]-3-{3-[4-(2-methoxy-ethyl)-piperazin-1-yl]-phenyl}-2,2-dimethyl-propionamide | | 522 | (300MHz, CDCl₃): 7.80(s, 1H), 7.50(t, 1H), 7.05(t, 1H), 6.78(m, 1H), 6.62(m, 1H), 6.50(m, 1H), 5.80(t, 1H), 4.18(d, 2H), 3.55(t, 2H), 3.37(s, 3H), 3.35(d, 2H), 3.18(m, 4H), 2.79(s, 2H), 2.66(m, 4H), 1.20(s, 6H), 1.02(s, 9H). |
| I-30 N-[2-Cyano-4-(2,2-dimethyl-propylamino)-pyrimidin-5-ylmethyl]-3-{3-[4-(2-ethoxy-ethyl)-piperazin-1-yl]-phenyl}-2,2-dimethyl-propionamide | | 536 | (300MHz, CDCl₃): 7.79(s, 1H), 7.50(t, 1H), 7.05(t, 1H), 6.78(m, 1H), 6.60(m, 1H), 6.49(m, 1H), 5.82(t, 1H), 4.17(d, 2H), 3.60(t, 2H), 3.53(q, 2H), 3.36(d, 2H), 3.18(m, 4H), 2.79(s, 2H), 2.68(m, 4H), 1.25(q, 3H), 1.20(s, 6H), 1.02(s, 9H). |

-continued

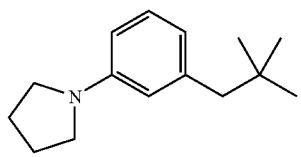

| Ex. | R | MS (ES+) (M + H)+ | 1H-NMR |
|---|---|---|---|
| I-31 N-[2-Cyano-4-(2,2-dimethyl-propylamino)-pyrimidin-5-ylmethyl]-2,2-dimethyl-3-(3-pyrrolidin-1-yl-phenyl)-propionamide | 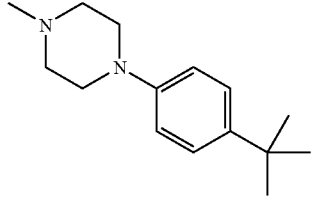 | 449 | (300MHz, CDCl$_3$): 7.79(s, 1H), 7.54(t, 1H), 7.0(t, 1H), 6.42(m, 1H), 6.34(m, 1H), 6.28(m, 1H), 5.84(t, 1H), 4.18(d, 2H), 3.34(d, 2H), 3.22(m, 4H), 2.79(s, 2H), 2.0(m, 4H), 1.22(s, 6H), 1.02(s, 9H). |
| I-32 N-[2-Cyano-4-(2,2-dimethyl-propylamino)-pyrimidin-5-ylmethyl]-2-[4-(4-methyl-piperazin-1-yl)-phenyl]-isobutyramide | 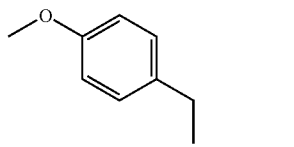 | 464 | (300MHz, CDCl$_3$): 7.76(s, 1H), 7.22(t, 1H), 7.15(d, 2H), 6.87(d, 2H), 5.61(t, 1H), 4.18(d, 2H), 3.24(d, 2H) 3.22(m, 4H), 2.58(m, 4H), 2.34(s, 3H), 1.53(s, 6H), 1.01(s, 9H). |
| I-33 N-[2-Cyano-4-(2,2-dimethyl-propylamino)-pyrimidin-5-ylmethyl]-2-(4-methoxy-phenyl)-acetamide | 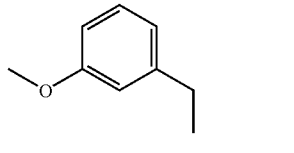 | 368 | (300MHz, CDCl$_3$): 7.81(s, 1H), 7.25(t, 1H), 7.13(d, 2H), 6.88(d, 2H), 5.85(t, 1H), 4.25(d, 2H), 3.81(s, 3H), 3.33(d, 2H), 0.99(s, 9H). |
| I-34 N-[2-Cyano-4-(2,2-dimethyl-propylamino)-pyrimidin-5-ylmethyl]-2-(3-methoxy-phenyl)-acetamide | 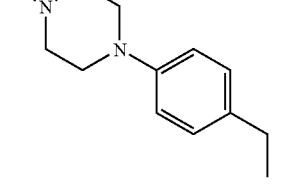 | 368 | (300MHz, CDCl$_3$): 7.82(s, 1H), 7.25(m, 2H), 6.87–6.74(m, 3H), 5.88 (t, 1H), 4.25(d, 2H), 3.81 (s, 3H), 3.33(d, 2H), 0.99 (s, 9H). |
| I-35 N-[2-Cyano-4-(2,2-dimethyl-propylamino)-pyrimidin-5-ylmethyl]-2-[4-(4-methyl-piperazin-1-yl)-phenyl]-acetamide | 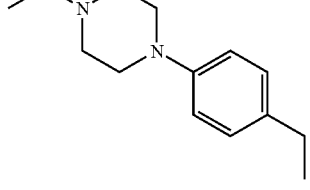 | 436 | (300MHz, CDCl$_3$): 7.80(s, 1H), 7.27(t, 1H), 7.06(d, 2H), 6.89(d, 2H), 5.82(t, 1H), 4.24(d, 2H), 3.54(s, 2H), 3.33(d, 2H), 3.22(m, 4H), 2.60(m, 4H), 2.46(q, 2H), 1.04(t, 3H), 1.0(s, 9H). |
| I-36 N-[2-Cyano-4-(2,2-dimethyl-propylamino)-pyrimidin-5-ylmethyl]-2-[4-(4-ethyl-piperazin-1-yl)-phenyl]-acetamide | | 450 | (300MHz, CDCl$_3$): 7.80(s, 1H), 7.27(t, 1H), 7.06(d, 2H), 6.89(d, 2H), 5.84(t, 1H), 4.22(d, 2H), 3.54(s, 2H), 3.34(d, 2H), 3.20(m, 4H), 2.58(m, 4H), 2.36(s, 3H), 1.0(s, 9H). |

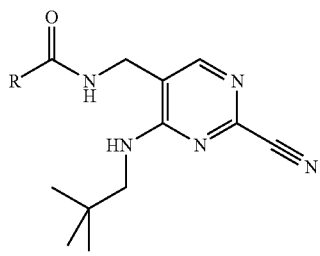

| Ex. | R | MS (ES+) (M + H)+ | 1H-NMR |
|---|---|---|---|
| I-37 N-[2-Cyano-4-(2,2-dimethyl-propylamino)-pyrimidin-5-ylmethyl]-2-[4-(4-isopropyl-piperazin-1-yl)-phenyl]-acetamide | | 464 | (300MHz, CDCl3): 7.80(s, 1H), 7.27(t, 1H), 7.06(d, 2H), 6.89(d, 2H), 5.83(t, 1H), 4.22(d, 2H), 3.54(s, 2H), 3.34(d, 2H), 3.21(m, 4H), 2.72(m, 1H), 2.67(m, 4H), 1.11(d, 6H), 0.98(s, 9H). |
| I-38 N-[2-Cyano-4-(2,2-dimethyl-propylamino)-pyrimidin-5-ylmethyl]-2-(4-pyrrolidin-1-yl-phenyl)-acetamide | | 407 | (300MHz, CDCl3): 7.79(s, 1H), 7.33(t, 1H), 7.02(d, 2H), 6.51(d, 2H), 5.85(t, 1H), 4.22(d, 2H), 3.50(s, 2H), 3.34(d, 2H), 3.26(m, 4H), 2.03(m, 4H), 1.0(s, 9H). |
| I-39 N-[2-Cyano-4-(2,2-dimethyl-propylamino)-pyrimidin-5-ylmethyl]-2-[4-(2-diethylamino-ethylamino)-phenyl]-isobutyramide | | 480 | (300MHz, CDCl3): 7.76(s, 1H), 7.34(t, 1H), 7.07(d, 2H), 6.58(d, 2H), 5.68(t, 1H), 4.48(t, broad, 1H), 4.18(d, 2H), 3.35(d, 2H), 3.10(t, 2H), 2.68(t, 2H), 2.54(q, 4H), 1.52(s, 6H), 1.03(m, 15H). |
| I-40 N-[2-Cyano-4-(2,2-dimethyl-propylamino)-pyrimidin-5-ylmethyl]-2-(4-pyrrolidin-1-yl-phenyl)-isobutyramide | | 435 | (300MHz, CDCl3): 7.75(s, 1H), 7.36(t, 1H), 7.12(d, 2H), 6.52(d, 2H), 5.66(t, 1H), 4.18(d, 2H), 3.34(s, 2H), 3.26(m, 4H), 2.00(m, 4H), 1.52(s, 6H), 1.0(s, 9H). |

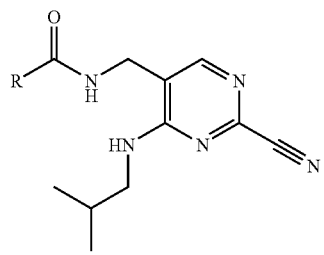

| Ex | R | MS (ES+) (M+H)+ | 1H-NMR |
|---|---|---|---|
| I-41 N-(2-Cyano-4-isobutylamino-pyrimidin-5-ylmethyl)-4-(4-methyl-piperazin-1-yl)-benzamide | | 408 | (300MHz, CDCl$_3$): 7.96(s, 1H), 7.70(t, 1H), 7.67(d, 2H), 6.89(d, 2H), 6.41(t, 1H), 4.50(d, 2H), 3.39–3.28(m, 6H), 2.56(m, 4H), 2.36 (s, 3H), 1.94(m, 1H), 0.94(d, 6H). |
| I-42 N-(2-Cyano-4-isobutylamino-pyrimidin-5-ylmethyl)-4-(4-ethyl-piperazin-1-yl)-benzamide | | 422 | (300MHz, CDCl$_3$): 7.90(s, 1H), 7.71(t, 1H), 7.67(d, 2H), 6.88(d, 2H), 6.52(t, 1H), 4.48(d, 2H), 3.38–3.28(m, 6H), 2.59(m, 4H), 2.48 (q, 2H), 1.94(m, 1H), 1.13(t, 3H), 0.94(d, 6H). |
| I-43 N-(2-Cyano-4-isobutylamino-pyrimidin-5-ylmethyl)-4-(4-isopropyl-piperazin-1-yl)-benzamide | | 436 | (300MHz, CDCl$_3$): 7.89(s, 1H), 7.80(t, 1H), 7.68(d, 2H), 6.88(d, 2H), 6.73(t, 1H), 4.48(d, 2H), 3.36–3.25(m, 6H), 2.74(m, 1H), 2.66 (m, 4H), 1.94(m, 1H), 1.09(d, 6H), 0.94(d, 6H). |
| I-44 N-(2-Cyano-4-isobutylamino-pyrimidin-5-ylmethyl)-4-(4-propyl-piperazin-1-yl)-benzamide | | 436 | (300MHz, CDCl$_3$): 7.90(s, 1H), 7.74(t, 1H), 7.68(d, 2H), 6.88(d, 2H), 6.57(t, 1H), 4.48(d, 2H), 3.36–3.26(m, 6H), 2.59(m, 4H), 2.35 (m, 2H), 1.95(m, 1H), 1.55(m, 2H), 0.94(d&t, 9H). |
| I-45 N-(2-Cyano-4-isobutylamino-pyrimidin-5-ylmethyl)-4-[4-(2-methoxy-ethyl)-piperazin-1-yl]-benzamide | | 452 | (300MHz, CDCl$_3$): 7.90(s, 1H), 7.74(t, 1H), 7.68(d, 2H), 6.88(d, 2H), 6.56(t, 1H), 4.49(d, 2H), 3.55(t, 2H), 3.38(s, 3H), 3.36–3.28(m, 6H), 2.64(m, 6H), 1.95(m, 1H), 0.93 (d, 6H) |

-continued

| Ex | R | MS (ES+) (M+H)+ | 1H-NMR |
|---|---|---|---|
| I-46 N-(2-Cyano-4-isobutylamino-pyrimidin-5-ylmethyl)-4-(1-propyl-piperidin-4-yl)-benzamide | | 435 | (300MHz, CDCl3): 7.91(s, 1H), 7.72 (d, 2H), 7.61(t, 1H), 7.30(d, 2H), 6.69(t, 1H), 4.51(d, 2H), 3.30(t, 2H), 3.08(d, broad, 2H), 2.56 (m, 1H), 2.35(m, 2H), 2.05(m, 2H), 1.94(m, 1H), 1.87–1.70(m, 4H), 1.56 (m, 2H), 0.95(d, 6H), 0.94(t, 3H). |
| I-47 N-(2-Cyano-4-isobutylamino-pyrimidin-5-ylmethyl)-4-[1-(2-methoxy-ethyl)-piperidin-4-yl]-benzamide | | 451 | (300MHz, CDCl3): 7.92(s, 1H), 7.70 (d, 2H), 7.63(t, 1H), 7.32(d, 2H), 6.73(t, 1H), 4.5(d, 2H), 3.54(t, 2H), 3.37(s, 3H), 3.30(t, 3H), 3.10(d, 2H), 2.62(t, 2H), 2.53(m, 1H), 2.13(m, 2H), 1.94 (m, 1H), 1.88–1.62 (m, 5H), 0.95(d, 6H). |
| I-48 4-(4-{[N-2-Cyano-4-isobutylamino-pyrimidin-5-ylmethyl]-carbamoyl}-phenyl)-4-piperazine-1-carboxylic acid tert-butyl ester | | 494 | (300MHz, CDCl3): 7.90(s, 1H), 7.72(t, 1H), 7.70(d, 2H), 6.88(d, 2H), 6.78(t, 1H), 4.48(d, 2H), 3.57(m, 4H), 3.28 (m, 6H), 1.94 (m, 1H), 1.49(s, 9H), 0.95(d, 6H). |
| I-49 N-(2-Cyano-4-isobutylamino-pyrimidin-5-ylmethyl)-4-piperazin-1-yl-benzamide | | 394 | (300MHz, CDCl3): 7.90(s, 1H), 7.72(t, 1H), 7.68(d, 2H), 6.88(d, 2H), 6.64(t, 1H), 4.48(d, 2H), 3.32–3.27(m, 6H), 3.02(m, 4H), 1.95 (m, 1H), 0.95(d, 6H). |

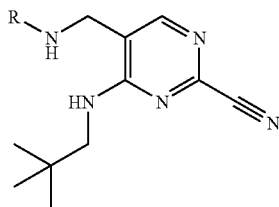

The following amine derivatives are obtained by dissolving (2-Chloro-5-chloromethyl-pyrimidin-4-yl)-(2,2-dimethyl-propyl)-amine (1B) and 1 equivalent of DIEA in DMF, cooling to 0° C. and adding 1 equivalent of the corresponding amine dropwise at 0° C. The reaction mixture is stirred at 0° C. for 12 h, then diluted with ethyl acetate and extracted once with brine. The organic layer is separated and dried over $Na_2SO_4$. The product is purified by flash chromatography.

| Ex | R | MS (ES+) (M+H)+ | 1H-NMR |
|---|---|---|---|
| I-50 4-(2,2-Dimethyl-propylamino)-5-[(4-methoxy-benzylamino)-methyl]-pyrimidine-2-carbonitrile | | 340 | (300MHz, CDCl3): 8.00(t, 1H), 7.84(s, 1H), 7.14(d, 2H), 6.86 (d, 2H), 3.80(s, 3H), 3.70(d, 2H), 3.30(d, 2H), 0.97(s, 9H). |
| I-51 4-(2,2-Dimethyl-propylamino)-5-[(3-methoxy-benzylamino)-methyl]-pyrimidine-2-carbonitrile | | 340 | (300MHz, CDCl$_3$): 7.94(t, 1H), 7.85(s, 1H), 7.24(m, 1H), 6.84–7.77(m, 3H), 3.80(s, 3H), 3.74(d, 2H), 3.32 (d, 2H), 0.98(s, 9H). |
| I-52 4-(2,2-Dimethyl-propylamino)-5-{[4-(4-methyl-piperazin-1-yl)-benzylamino]-methyl}-pyrimidine-2-carbonitrile | | 408 | (300MHz, CDCl$_3$): 8.04(t, 1H), 7.82(s, 1H), 7.12(d, 2H), 6.89 (d, 2H), 3.74(s, 2H), 3.65(s, 2H), 3.31(d, 2H), 3.22(m, 4H), 2.60 (m, 4H), 2.37(s, 3H), 0.97(s, 9H). |
| I-53 4-(2,2-Dimethyl-propylamino)-5-({4-[4-(2-ethoxy-ethyl)-piperazin-1-yl]-benzylamino}-methyl)-pyrimidine-2-carbonitrile | | 466 | (300MHz, CDCl$_3$): 8.03(t, 1H), 7.82(s, 1H), 7.13(d, 2H), 6.89 (d, 2H), 3.73(s, 2H), 3.65(s, 2H), 3.61(t, 2H), 3.54(q, 2H), 3.31 (d, 2H), 3.22(m, 4H), 2.70–2.64(m, 6H), 1.33(t, 3H), 0.97(s, 9H). |
| I-54 4-(2,2-Dimethyl-propylamino)-5-[(1-methyl-1-phenyl-ethylamino)-methyl]-pyrimidine-2-carbonitrile | | 338 | (300MHz, CDCl$_3$): 7.88(s, 1H), 7.80(t, 1H), 7.37(m, 5H), (s, 1H), 7.29(t, 1H), 3.41 (s, 2H), 3.34(d, 2H), 1.55(s, 6H), 1.01(s, 9H). |
| I-55 4-(2,2-Dimethyl-propylamino)-5-{[2-(4-methoxy-phenyl)-1,1-dimethyl-ethylamino]-methyl}-pyrimidine-2-carbonitrile | | 382 | (300MHz, CDCl$_3$): 7.95(t, 1H), 7.88 (s, 1H), 7.03(d, 2H), 6.83(d, 2H), 3.80(s, 3H), 3.74(s, 2H), 3.27 (d, 2H), 2.70(s, 2H), 1.15(s, 6H), 0.95(s, 9H). |

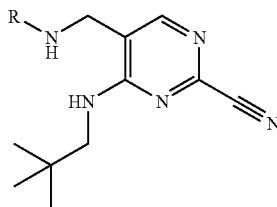

The following amine derivatives are obtained by dissolving (2-Chloro-5-chloromethyl-pyrimidin-4-yl)-(2,2-dimethyl-propyl)-amine (1B) and 1 equivalent of DIEA in DMF, cooling to 0° C. and adding 1 equivalent of the corresponding amine dropwise at 0° C. The reaction mixture is stirred at 0° C. for 12 h, then diluted with ethyl acetate and extracted once with brine. The organic layer is separated and dried over $Na_2SO_4$. The product is purified by flash chromatography.

| Ex | R | MS (ES+) (M+H)+ | 1H-NMR |
|---|---|---|---|
| I-56 4-(2,2-Dimethyl-propylamino)-5-{[2-(4-fluoro-phenyl)-1,1-dimethyl-ethylamino]-methyl}-pyrimidine-2-carbonitrile | | 370 | (300MHz, $CDCl_3$): 7.90(s, 1H), 7.85(t, 1H), 7.10–6.94(m, 4H), 3.75(s, 2H), 3.28 (d, 2H), 2.74(s, 2H), 1.17(s, 6H), 0.95(s, 9H). |
| I-57 5-({1,1-Dimethyl-2-[4-(4-methyl-piperazin-1-yl)-phenyl]-ethylamino}-methyl)-4-(2,2-dimethyl-propylamino)-pyrimidine-2-carbonitrile | | 450 | (300MHz, $CDCl_3$): 8.00(t, 1H), 7.87(s, 1H), 7.00(d, 2H), 6.85 (d, 2H), 3.74(s, 2H), 3.26(d, 2H), 3.18(m, 4H), 2.62(s, 3H), 2.58 (m, 4H), 2.35(s, 2H), 1.14(s, 6H), 0.95(s, 9H). |
| I-58 4-(2,2-Dimethyl-propylamino)-5-({2-[4-(4-isopropyl-piperazin-1-yl)-phenyl]-1,1-dimethyl-ethylamino}-methyl)-pyrimidine-2-carbonitrile | | 478 | (300MHz, $CDCl_3$): 8.00(t, 1H), 7.87(s, 1H), 6.99(d, 2H), 6.84 (d, 2H), 3.74(d, 2H), 3.27(d, 2H), 3.18(m, 4H), 2.70(m, 1H), 2.68 (m, 6H), 1.15(s, 6H), 1.10(d, 6H), 0.95(s, 9H). |
| I-59 4-(2,2-Dimethyl-propylamino)-5-[(2-{4-[4-(2-methoxy-ethyl)-piperazin-1-yl]-phenyl}-1,1-dimethyl-ethylamino)-methyl]-pyrimidine-2-carbonitrile | | 494 | (300MHz, $CDCl_3$): 8.00(t, 1H), 7.88(s, 1H), 7.00(d, 2H), 6.83 (d, 2H), 3.72(s, 2H), 3.55(t, 2H), 3.37(s, 3H), 3.27(d, 2H), 3.20 (m, 4H), 2.68–2.60 (m, 8H), 1.15(s, 6H), 0.95(s, 9H). |

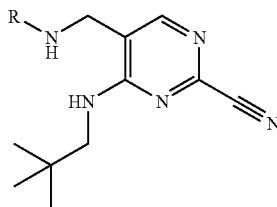

The following amine derivatives are obtained by dissolving (2-Chloro-5-chloromethyl-pyrimidin-4-yl)-(2,2-dimethyl-propyl)-amine (1B) and 1 equivalent of DIEA in DMF, cooling to 0° C. and adding 1 equivalent of the corresponding amine dropwise at 0° C.

The reaction mixture is stirred at 0° C. for 12 h, then diluted with ethyl acetate and extracted once with brine. The organic layer is separated and dried over $Na_2SO_4$. The product is purified by flash chromatography.

| Ex | R | MS (ES+) (M+H)+ | 1H-NMR |
|---|---|---|---|
| I-60 4-(2,2-Dimethyl-propylamino)-5-[(2-{3-[4-(2-ethoxy-ethyl)-piperazin-1-yl]-phenyl}-1,1-dimethyl-ethylamino)-methyl]-pyrimidine-2-carbonitrile | | 508 | (300MHz, CDCl₃): 8.00(t, 1H), 7.88(s, 1H), 7.00(d, 2H), 6.83 (d, 2H), 3.72(s, 2H), 3.55(t, 2H), 3.36(q, 2H), 3.27(d, 2H), 3.20 (m, 4H), 2.68–2.60 (m, 8H), 1.18(t, 3H), 1.15(s, 6H), 0.95(s, 9H). |
| I-61 4-(2,2-Dimethyl-propylamino)-5-({2-[3-(4-ethyl-piperazin-1-yl)-phenyl]-1,1-dimethyl-ethylamino}-methyl)-pyrimidine-2-carbonitrile | | 464 | (300MHz, CDCl₃): 8.00(t, 1H), 7.88(s, 1H), 7.16(m, 1H), 6.81(m, 1H), 6.63–6.60(m, 2H), 3.74(d, 2H), 3.27(d, 2H), 3.17 (m, 4H), 2.71(s, 3H), 2.59(m, 4H), 2.48(q, 2H), 1.17(s, 6H), 1.14 (t, 3H), 0.95(s, 9H). |
| I-62 4-(2,2-Dimethyl-propylamino)-5-({2-[3-(4-isopropyl-piperazin-1-yl)-phenyl]-1,1-dimethyl-ethylamino}-methyl)-pyrimidine-2-carbonitrile | | 478 | (300MHz, CDCl₃): 8.00(t, 1H), 7.88(s, 1H), 7.16(m, 1H), 6.83(m, 1H), 6.63–6.58(m, 2H), 3.75(s, 2H), 3.27(d, 2H), 3.17 (m, 4H), 2.73–2.64 (m, 7H), 1.17(s, 6H), 1.10(d, 6H), 0.95(s, 9H). |
| I-63 4-(2,2-Dimethyl-propylamino)-5-{[1,1-dimethyl-2-(3-pyrrolidin-1-yl-phenyl)-ethylamino]-methyl}-pyrimidine-2-carbonitrile | | 421 | (300MHz, CDCl₃): 8.08(t, 1H), 7.88(s, 1H), 7.12(m, 1H), 6.43–6.38(m, 2H), 6.26(s, 1H), 3.76(s, 2H), 3.27–3.20(m, 6H), 2.72(s, 2H), 2.00 (m, 4H), 1.18(s, 6H), 0.95(s, 9H). |

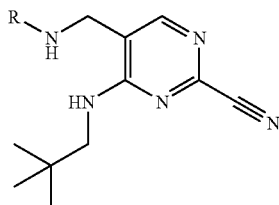

The following amine derivatives are obtained by dissolving (2-Chloro-5-chloromethyl-pyrimidin-4-yl)-(2,2-dimethyl-propyl)-amine (1B) and 1 equivalent of DIEA in DMF, cooling to 0° C. and adding 1 equivalent of the corresponding amine dropwise at 0° C. The reaction mixture is stirred at 0° C. for 12 h, then diluted with ethyl acetate and extracted once with brine. The organic layer is separated and dried over $Na_2SO_4$. The product is purified by flash chromatography.

| Ex | R | MS (ES+) (M+H)+ | 1H-NMR |
|---|---|---|---|
| I-64 4-(2,2-Dimethyl-propylamino)-5-[(2-{3-[4-(2-methoxy-ethyl)-piperazin-1-yl]-phenyl}-1,1-dimethyl-ethylamino)-methyl]-pyrimidine-2-carbonitrile | | 494 | (300MHz, CDCl₃): 8.00(t, 1H), 7.88(s, 1H), 7.16(m, 1H), 6.80(m, 1H), 6.63–6.58(m, 2H), 3.75(s, 2H), 3.55(t, 2H), 3.37(s, 3H), 3.27(d, 2H), 3.18(m, 4H), 2.72(s, 2H), 2.68–2.60(m, 6H), 1.17(s, 6H), 0.95(s, 9H). |
| I-65 4-(2,2-Dimethyl-propylamino)-5-{[2-(4-methoxy-phenyl)-ethylamino]-methyl}-pyrimidine-2-carbonitrile | | 354 | (300MHz, CDCl₃): 8.05(t, 1H), 7.84(s, 1H), 7.06(d, 2H), 6.84(d, 2H), 3.80(s, 3H), 3.75(s, 2H), 3.25(d, 2H), 2.77(m, 4H), 0.97(s, 9H). |
| I-66 4-(2,2-Dimethyl-propylamino)-5-({2-[4-(4-methyl-piperazin-1-yl)-phenyl]-ethylamino}-methyl)-pyrimidine-2-carbonitrile | | 422 | (300MHz, CDCl₃): 8.10(t, 1H), 7.84(s, 1H), 7.05(d, 2H), 6.89(d, 2H), 3.73(s, 2H), 3.26(d, 2H), 3.18(m, 4H), 2.83–2.70(m, 4H), 2.50(m, 4H), 2.36(s, 3H), 0.99(s, 9H). |
| I-67 4-(2,2-Dimethyl-propylamino)-5-({2-[4-(4-isopropyl-piperazin-1-yl)-phenyl]-ethylamino}-methyl)-pyrimidine-2-carbonitrile | | 450 | (300MHz, CDCl₃): 8.10(t, 1H), 7.82(s, 1H), 7.04(d, 2H), 6.89(d, 2H), 3.73(s, 2H), 3.27(d, 2H), 3.18(m, 4H), 2.84–2.68(m, 7H), 1.12(d, 6H), 0.99(s, 9H). |
| I-68 4-(2,2-Dimethyl-propylamino)-5-[(2-{4-[4-(2-methoxy-ethyl)-piperazin-1-yl]-phenyl}-ethylamino)-methyl]-pyrimidine-2-carbonitrile | | 466 | (300MHz, CDCl₃): 8.10(t, 1H), 7.82(s, 1H), 7.04(d, 2H), 6.86(d, 2H), 3.75(s, 2H), 3.38(s, 3H), 3.30–3.19(m, 6H), 2.82–2.60(m, 11H), 0.96(s, 9H). |

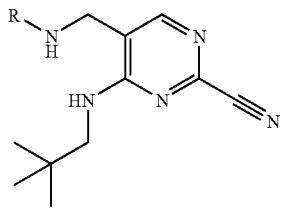

The following amine derivatives are obtained by dissolving (2-Chloro-5-chloromethyl-pyrimidin-4-yl)-(2,2-dimethyl-propyl)-amine (1B) and 1 equivalent of DIEA in DMF, cooling to 0° C. and adding 1 equivalent of the corresponding amine dropwise at 0° C. The reaction mixture is stirred at 0° C. for 12 h, then diluted with ethyl acetate and extracted once with brine. The organic layer is separated and dried over $Na_2SO_4$. The product is purified by flash chromatography.

| Ex | R | MS (ES+) (M+H)+ | 1H-NMR |
|---|---|---|---|
| I-69 4-(2,2-Dimethyl-propylamino)-5-{[2-(3-methoxy-phenyl)-ethylamino]-methyl}-pyrimidine-2-carbonitrile | | 354 | (300MHz, CDCl₃): 8.03(t, 1H), 7.82(s, 1H), 7.20(m, 1H), 6.80–6.70(m, 3H), 3.80(s, 3H), 3.75(s, 2H), 3.26 (d, 2H), 2.80(m, 4H), 0.96(s, 9H). |
| I-70 4-(2,2-Dimethyl-propylamino)-5-({2-[3-(4-methyl-piperazin-1-yl)-phenyl]-ethylamino}-methyl)-pyrimidine-2-carbonitrile | | 422 | (300MHz, CDCl₃): 8.07(t, 1H), 7.82(s, 1H), 7.18(m, 1H), 6.80–6.20(m, 3H), 3.75(s, 2H), 3.28(d, 2H), 3.22 (m, 4H), 2.80(m, 4H), 2.60(m, 4H), 2.37(s, 3H), 0.97(s, 9H). |
| I-71 4-(2,2-Dimethyl-propylamino)-5-({2-[4-(4-isopropyl-piperazin-1-yl)-phenyl]-ethylamino}-methyl)-pyrimidine-2-carbonitrile | | 450 | (300MHz, CDCl₃): 8.07(t, 1H), 7.85(s, 1H), 7.19(m, 1H), 6.82–6.65(m, 3H), 3.75(s, 2H), 3.29(d, 2H), 3.22 (m, 4H), 2.86–2.70 (m, 6H), 1.13(d, 6H), 0.99(s, 9H). |
| I-72 4-(2,2-Dimethyl-propylamino)-5-[(2-pyrrol-1-yl-ethylamino)-methyl]-pyrimidine-2-carbonitrile | | 313 | (300MHz, CDCl₃): 7.82(s, 1H), 7.72(t, 1H), 6.3(m, 2H), 6.17 (m, 2H), 4.02(t, 2H), 3.72(s, 2H), 3.30(d, 2H), 2.91(m, 2H), 0.99 (s, 9H). |
| I-73 4-(2,2-Dimethyl-propylamino)-5-[(3-piperidin-1-yl-propylamino)-methyl]-pyrimidine-2-carbonitrile | | 345 | (300MHz, CDCl₃): 7.92(s, 1H), 7.80(t, 1H), 3.75(s, 2H), 3.30 (s, 2H), 2.94–2.59(m, 8H), 2.06–1.82(m, 6H), 1.60(m, 2H), 0.994(s, (H). |

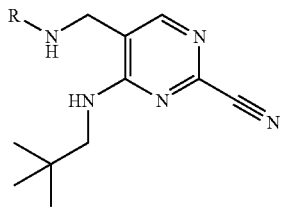

The following amine derivatives are obtained by dissolving (2-Chloro-5-chloromethyl-pyrimidin-4-yl)-(2,2-dimethyl-propyl)-amine (1B) and 1 equivalent of DIEA in DMF, cooling to 0° C. and adding 1 equivalent of the corresponding amine dropwise at 0° C. The reaction mixture is stirred at 0° C. for 12 h, then diluted with ethyl acetate and extracted once with brine. The organic layer is separated and dried over $Na_2SO_4$. The product is purified by flash chromatography.

| Ex | R | MS (ES+) (M+H)+ | 1H-NMR |
|---|---|---|---|
| I-74 4-(2,2-Dimethyl-propylamino)-5-{[2-(4-methoxy-phenyl)-2-methyl-propylamino]-methyl}-pyrimidine-2-carbonitrile | | 382 | (300MHz, CDCl₃): 7.81(s, 1H), 7.77(t, 1H), 7.21(d, 2H), 6.85 (d, 2H), 3.80(s, 3H), 3.63(s, 2H), 3.23 (d, 2H), 2.65(s, 2H), 1.30(s, 6H), 0.92(s, 9H). |
| I-75 4-(2,2-Dimethyl-propylamino)-5-({2-methyl-2-[4-(4-methyl-piperazin-1-yl)-phenyl]-propylamino}-methyl)-pyrimidine-2-carbonitrile | | 450 | (300MHz, CDCl₃): 7.84(t, 1H), 7.81(s, 1H), 7.18(d, 2H), 6.88 (d, 2H), 3.63(s, 2H), 3.28–3.21(m, 6H), 2.63(s, 2H), 2.60(m, 4H), 2.37(s, 3H), 1.30 (s, 6H), 0.94(s, 9H). |
| I-76 4-(2,2-Dimethyl-propylamino)-5-({2-[4-(4-isopropyl-piperazin-1-yl)-phenyl]-2-methyl-propylamino}-methyl)-pyrimidine-2-carbonitrile | | 478 | (300MHz, CDCl₃): 7.85(t, 1H), 7.80(s, 1H), 7.19(d, 2H), 6.88 (d, 2H), 3.63(s, 2H), 3.26–3.18(m, 6H), 2.75–2.60(m, 7H), 1.30(s, 6H), 1.11(d, 6H), 0.94(s, 9H). |
| I-77 4-(2,2-Dimethyl-propylamino)-5-[(2-{4-[4-(2-ethoxy-ethyl)-piperazin-1-yl]-phenyl}-2-methyl-propylamino)-methyl]-pyrimidine-2-carbonitrile | | 508 | (300MHz, CDCl₃): 7.84(t, 1H), 7.80(s, 1H), 7.19(d, 2H), 6.87 (d, 2H), 3.63–3.59(m, 4H), 3.53(q, 2H), 3.26–3.18(m, 6H), 2.70–2.60(m, 8H), 1.30(s, 6H), 1.23(t, 6H), 0.94 (s, 9H). |
| I-78 N-(2-Cyano-4-isobutylamino-pyrimidin-5-ylmethyl)-4-(4-isopropyl-piperazin-1-yl)-benzamide | | 435 | (300MHz, CDCl₃): 7.87(t, 1H), 7.80(s, 1H), 7.19(d, 2H), 6.88 (d, 2H), 3.61(s, 2H), 2.35(d, 2H), 3.14 (m, 4H), 2.63(s, 2H), 1.72(m, 4H), 1.58(m, 2H), 1.30(s, 6H), 0.94 (s, 9H). |

-continued

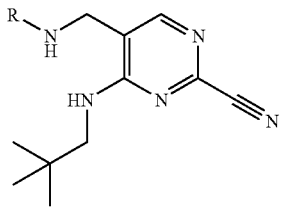

The following amine derivatives are obtained by dissolving (2-Chloro-5-chloromethyl-pyrimidin-4-yl)-(2,2-dimethyl-propyl)-amine (1B) and 1 equivalent of DIEA in DMF, cooling to 0° C. and adding 1 equivalent of the corresponding amine dropwise at 0° C. The reaction mixture is stirred at 0° C. for 12 h, then diluted with ethyl acetate and extracted once with brine. The organic layer is separated and dried over $Na_2SO_4$. The product is purified by flash chromatography.

| Ex | R | MS (ES+) (M+H)+ | 1H-NMR |
|---|---|---|---|
| I-79 4-(2,2-Dimethyl-propylamino)-5-[4-(3-methoxy-phenyl)-piperazin-1-ylmethyl]-pyrimidine-2-carbonitrile | (3-methoxyphenyl piperazine with N-ethyl) | 395 | (300MHz, $CDCl_3$): 7.93(s, 1H), 7.81(t, 1H), 7.19(m, 1H), 6.56–6.43 m, 3H), 3.79(s, 3H), 3.51(s, 2H), 3.32 (d, 2H), 3.19(m, 4H), 2.62(m, 4H), 0.98(s, 9H). |
| I-80 4-(2,2-Dimethyl-propylamino)-5-[4-(4-methoxy-phenyl)-piperazin-1-ylmethyl]-pyrimidine-2-carbonitrile | (4-methoxyphenyl piperazine with N-ethyl) | 395 | (300MHz, $CDCl_3$): 7.93(s, 1H), 7.85(t, 1H), 6.88(2d, 4H), 3.79(s, 3H), 3.51(s, 2H), 3.32(d, 2H), 3.10 (m, 4H), 2.62(m, 4H), 0.98(s, 9H). |
| I-81 4-(2,2-Dimethyl-propylamino)-5-{[1-methyl-1-(1-phenyl-cyclopropyl)-ethylamino]-methyl}-pyrimidine-2-carbonitrile | (1-phenylcyclopropyl-t-butyl) | 378 | (300MHz, $CDCl_3$): 7.91(s, 1H), 7.80(s, 1H), 7.34–7.21(m, 5H), 3.83(s, 2H), 3.19 (d, 2H), 1.11(s, 6H) 0.96(q, 2H), 0.86(s, 9H), 0.77(q, 2H). |

The piperazinyl-benzoic acid precursors used in the preparation of the above compounds may be prepared substantially as described below for the reference 4-[4-[(2-methoxy-ethyl)-piperazin-1-yl]benzoic acid precusor.

Preparation of piperazinyl-benzoic acids

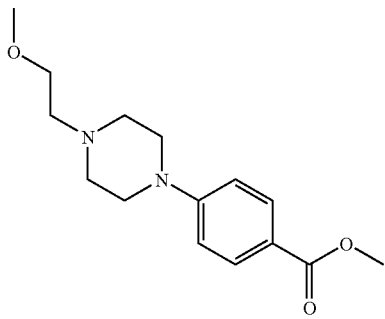

A) 4-[4-(2-Methoxy-ethyl)-piperazin-1-yl]benzoic acid methyl ester

To 10 ml of 1,4-dioxan is added 0.645 g (3.0 mmol) of methyl-4-bromobenzoate 0.519 g (3.6 mmol) of 1-(2-methoxy-ethyl-piperazine, 0.892 g (8.47 mmol) of potassium phosphate, 0.177 g (0.45 mmol) of 2-dicycohexylphosphino-2'-(N,N-dimethylamino)biphenyl and 0.137 g (0.15 mmol) tris-(benzylideneacetone)palladium (0). The resulting reaction mixture is stirred under argon for 5 hours at 100° C., then cooled to room temperature, diluted with ethyl acetate and filtered. The filtrate is washed once with $H_2O$ and once with brine, the organic layer separated and dried over $Na_2SO_4$. Purification of the crude product by flash chromatography (dichloromethane/methanol) yields 0.52 g of 4-[4-(2-methoxy-ethyl)-piperazin-1-yl)]benzoic acid methyl ester as a solid.

MS (ES+): 279 (M+H)+

1H-NMR (300 MHz, $CDCl_3$): 7.94 (d, 2H), 6.87 (d, 2H), 3.88 (s, 3H), 3.55 (t, 2H), 3.38 (s, 3H), 3.36 (m, 4H), 2.68 (m, 6H).

B) 4-[4-(2-Methoxy-ethyl)-piperazin-1-yl)-benzoic acid sodium salt

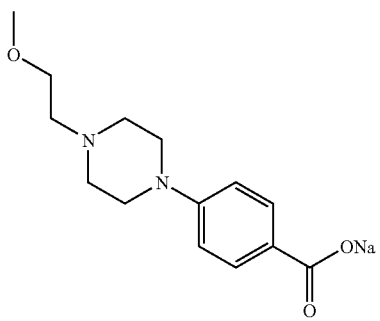

To 4 ml of MeOH/H$_2$O (1:1) is added 0.52 g (1.87 mmol) of 4-[4-(2-methoxy-ethyl)-piperazin-1-yl]benzoic acid methyl ester and 0.078 g (1.96 mmol) of NaOH (30%). The resulting reaction mixture is stirred 1 hour at 80° C., then cooled to room temperature and diluted with H$_2$O. The H$_2$O-layer is extracted 3 times with diethyl ether and then lyophilised to yield 0.47 g of 4-[4-(2-methoxy-ethyl)-piperazin-1-yl)-benzoic acid sodium salt as a white solid.

MS (ES+): 265 (M+H)$^+$ $^1$H-NMR (300 MHz, CD$_3$OD): 7.97 (d, 2H), 7.04 (d, 2H), 3.72 (t, 2H), 3.50 (s, 3H), 3.42 (m, 4H), 2.82 (m, 6H).

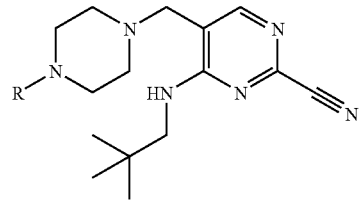

| Ex | R | MS (ES+) (M+H)$^+$ | $^1$H-NMR |
|---|---|---|---|
| I-82 4-(2,2-Dimethyl-propylamino)-5-[4-(2-pyridin-4-yl-ethyl)-piperazin-1-ylmethyl]-pyrimidine-2-carbonitrile | 4-pyridyl-CH$_2$CH$_2$- | 394 | (300MHz, CDCl$_3$): 8.50(d, 2H), 7.89(s, 1H), 7.83(t, 1H), 7.13 (d, 2H), 3.45(s, 2H), 3.31(d, 2H), 2.78(m, 2H), 2.65–2.40(m, 10H), 0.99(s, 9H). |
| I-83 4-(2,2-Dimethyl-propylamino)-5-[4-(2-pyridin-2-yl-ethyl)-piperazin-1-ylmethyl]-pyrimidine-2-carbonitrile | 2-pyridyl-CH$_2$CH$_2$- | 394 | (300MHz, CDCl$_3$): 8.50(d, 1H), 7.88(s& t, 2H), 7.59(t, 1H), 7.19–7.10(m, 2H), 3.45(s, 2H), 3.31(d, 2H), 2.95(m, 2H), 2.78 (m, 2H), 2.60–2.41(m, broad, 8H), 0.99(s, 9H). |
| I-84 4-(2,2-Dimethyl-propylamino)-5-(4-pyridin-4-ylmethyl-piperazin-1-ylmethyl)-pyrimidine-2-carbonitrile | 4-pyridyl-CH$_2$- | 380 | (300MHz, CDCl$_3$): 8.53(d, 2H), 7.89 s, 1H), 7.84(t, 1H), 7.27 (d, 2H), 3.52(s, 2H), 3.46(s, 2H), 3.30(d, 2H), 2.60–2.40(m, broad, 8H), 0.99(s, 9H). |
| I-85 4-(2,2-Dimethyl-propylamino)-5-[4-(2-piperidin-1-yl-ethyl)-piperazin-1-ylmethyl]-pyrimidine-2-carbonitrile | piperidyl-CH$_2$CH$_2$- | 400 | (300MHz, CDCl$_3$): 7.85(s&t, 2H), 3.44 (s, 2H), 3.30(d, 2H), 2.60–2.38(m, 16H), 1.60(m, 4H), 1.45(m, 2H), 0.99(s, 9H). |

-continued

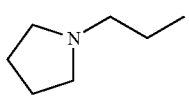

| Ex | R | MS (ES+) (M+H)+ | 1H-NMR |
|---|---|---|---|
| I-86 4-(2,2-Dimethyl-propylamino)-5-[4-(2-pyrrolidin-1-yl-ethyl)-piperazin-1-ylmethyl]-pyrimidine-2-carbonitrile | 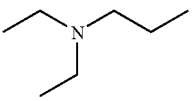 | 386 | (300MHz, CDCl$_3$): 7.86(s&t, 2H), 3.44 (s, 2H), 3.31(d, 2H), 2.70–2.40(m, 16H), 1.82(m, 4H), 1.00(s, 9H). |
| I-87 5-[4-(2-Diethylamino-ethyl)-piperazin-1-ylmethyl]-4-(2,2-dimethyl-propylamino)-pyrimidine-2-carbonitrile | 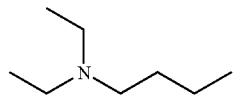 | 388 | (300MHz, CDCl$_3$): 7.89(s&t, 2H), 3.44 (s, 2H), 3.31(d, 2H), 2.64–2.42(m, 16H), 1.06(t, 6H), 1.00(s, 9H). |
| I-88 5-[4-(3-Diethylamino-propyl)-piperazin-1-ylmethyl]-4-(2,2-dimethyl-propylamino)-pyrimidine-2-carbonitrile |  | 402 | (300MHz, CDCl$_3$): 7.89(s&t, 2H)3.44 (s, 2H), 3.30(d, 2H), 2.60–2.32(m, 16H), 1.67(m, 2H), 1.06(t, 6H), 1.00(s, 9H). |
| I-89 4-(2,2-Dimethyl-propylamino)-5-[4-(1-methyl-piperidin-4-yl)-piperazin-1-ylmethyl]-pyrimidine-2-carbonitrile | 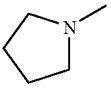 | 386 | (300MHz, CDCl$_3$): 7.92(t, 1H), 7.89(s, 1H), 3.44(s, 2H), 3.29 (d, 2H), 2.95(d, broad, 2H), 2.64–2.41(m, broad, 8H), 2.29(s, 3H), 2.25(m, 2H), 2.20–1.59(m, 5H), 0.99(s, 9H). |
| I-90 4-(2,2-Dimethyl-propylamino)-5-(4-pyrrolidin-1-yl-piperidin-1-ylmethyl)-pyrimidine-2-carbonitrile | 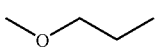 | 357 | (300MHz, CDCl$_3$): 7.96(t, 1H), 7.85(s, 1H), 3.44(s, 2H), 3.29 (d, 2H), 2.85(d, broad, 2H), 2.60(m, broad, 4H), 2.05(m, 3H), 1.99–1.50(m, 8H), 0.98(s, 9H). |
| I-91 4-(2,2-Dimethyl-propylamino)-5-[4-(2-methoxy-ethyl)-piperazin-1-ylmethyl]-pyrimidine-2-carbonitrile | | 347 | (300MHz, CDCl$_3$): 7.87(s&t, 2H)3.50 (t, 2H), 3.45(s, 2H), 3.34(s, 3H), 3.30(d, 2H), 2.62–2.48(m, broad, 10H), 1.00(s, 9H). |

Example II describes the preparation of 5-amido substituted-pyrimidine-2-carbonitriles Example II-1

2-Cyano-4-(2,2-dimethyl-propylamino)-pyrimidine-5-carboxylic acid 4-methoxy-benzylamide

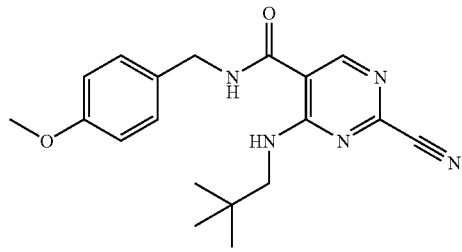

A. 2-Chloro-4-(2,2-dimethyl-propylamino)-pyrimidine-5-carbaldehyde

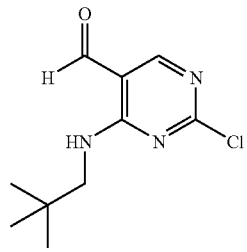

To a solution of (5-bromo-2-chloro-pyrimidin-4-yl)-(2,2-dimethyl-propyl)-amine (30 g, 108 mmol) in THF (500 ml) is added n-butyllithium (1.6 mol/l in n-hexane, 148 ml, 237 mmol) dropwise at −78° C. and the mixture is stirred for 10 min. Ethylformate (19 ml, 230 mol) is added dropwise to the mixture at −78° C., and the reaction mixture is allowed to warm to ambient temperature. After being stirred for 1 hour, the reaction mixture is quenched with saturated NH$_4$Cl at −78° C. and then extracted with AcOEt. The combined extracts are washed with water, brine, dried over MgSO$_4$ and concentrated under reduced pressure. The residue is purified by silica gel column chromatography (eluent:n-hexane:AcOEt=4:1) give 2-chloro-4-(2,2-dimethyl-propylamino)-pyrimidine-5-carbaldehyde. Rf=0.56 (n-hexane:AcOEt=1:1). $^1$H NMR (400 MHz, DMSO-d$_6$) δ 1.00 (s, 9H), 3.41 (d, 2H), 8.40 (s, 1H), 8.88 (brs, 1H), 9.84 (s, 1H).

B. 2-Chloro-4-(2,2-dimethyl-propylamino)-pyrimidine-5-carboxylic acid 4-methoxy-benzylamide

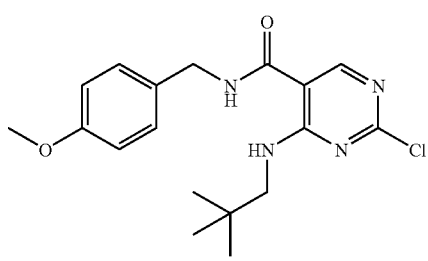

To a solution of 2-chloro-4-(2,2-dimethyl-propylamino)-pyrimidine-5-carbaldehyde (1.2 g, 5.27 mmol) in THF (20 ml) is added sulfamic acid (0.819 g, 8.4 mmol) at ambient temperature. To the mixture, sodium chlorite (1.43 g, 15.8 mmol) in water (10 ml) is added dropwise at 0° C. and the reaction mixture is allowed to warm to ambient temperature. After being stirred for 30 min. at ambient temperature, the reaction mixture is diluted with water and extracted with CH$_2$Cl$_2$. The combined extracts are washed with water, brine, dried over MgSO$_4$ and concentrated under reduced pressure to afford crude acid (1.17 g). To a solution of the crude acid (0.5 g, 2.05 mmol) in CH$_2$Cl$_2$ (10 ml) are added oxalyl chloride (0.36 ml, 4.1 mmol) and catalytic amount of DMF successively at 0° C., and the mixture is allowed to warm to ambient temperature. After being stirred for 1 hour at ambient temperature, the mixture is transferred to a solution of p-methoxybenzylamine (2.25 g, 16.7 mmol) in THF (30 ml) at −10° C.−−20° C. and the reaction mixture is stirred for 1 hour. The reaction mixture is quenched with cold water and extracted with CH$_2$Cl$_2$. The combined extracts are washed with water, brine, dried over MgSO$_4$ and concentrated under reduced pressure. The residue is purified by silica gel column chromatography (eluent:n-hexane:AcOEt=2:1) give 2-chloro-4-(2,2-dimethyl-propylamino)-pyrimidine-5-carboxylic acid 4-methoxy-benzylamide. Rf=0.38 (n-hexane:AcOEt=2:1). $^1$H NMR (400 MHz, DMSO-d$_6$) δ 1.01 (s, 9H), 3.35 (d, 2H), 3.81 (s, 3H), 4.52 (d, 2H), 6.23 (brs, 1H), 6.90 (d, 2H), 7.25 (d, 2H), 8.15 (s, 1H), 9.09 (brs, 1H).

C. 2-Cyano-4-(2,2-dimethyl-propylamino)-pyrimidine-5-carboxylic acid 4-methoxy-benzylamide

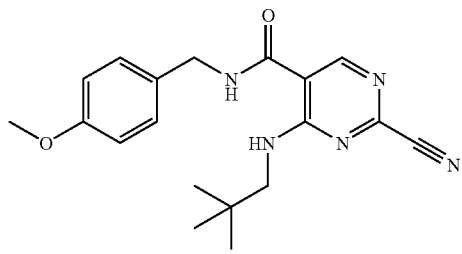

To a solution of NaCN (95 mg, 1.9 mmol) in water (1 ml) and DMSO (10 ml) are added 1,4-diazabicyclo[2,2,2]octane (48 mg, 0.43 mmol) and 2-chloro-4-(2,2-dimethyl-propylamino)-pyrimidine-5-carboxylic acid 4-methoxy-benzylamide (470 mg, 1.3 mmol) in DMSO (2 ml) successively at ambient temperature. After being stirred for 2 hours at 50° C., the reaction mixture is poured into cold water and extracted with AcOEt. The combined extracts are washed with water, brine and dried over MgSO$_4$. The concentrated residue is purified by silica gel column chromatography (eluent:n-hexane:AcOEt=2:1) give 2-cyano-4-(2,2-dimethyl-propylamino)-pyrimidine-5-carboxylic acid 4-methoxy-benzylamide. Rf=0.45 (n-hexane:AcOEt=2:1). $^1$H NMR (400 MHz, DMSO-d$_6$) δ 1.00 (s, 9H), 3.37 (d, 2H), 3.81 (s, 3H), 4.53 (d, 2H), 6.36 (brs, 1H), 6.89 (d, 2H), 7.25 (d, 2H), 8.28 (s, 1H), 9.08 (brs, 1H).

11-2

2-Cyano-4-(2,2-dimethyl-propylamino)-pyrimidine-5-carboxylic acid (5-methyl-2-phenyl-2.H.-pyrazol-3-yl)-amide

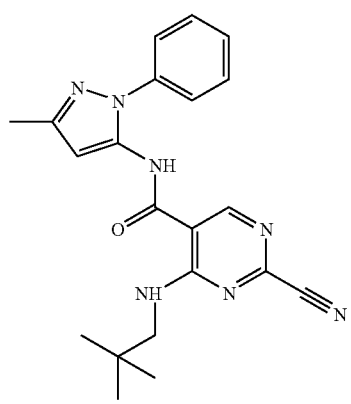

A. 2-Chloro-4-(2,2-dimethyl-propylamino)-pyrimidine-5-carboxylic acid

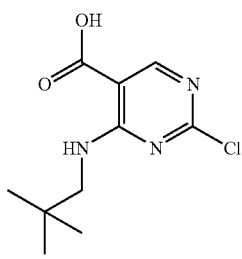

To a solution of 2,4-Dichloro-pyrimidine-5-carboxylic acid (1.04 g, 5.39 mmol) and triethylamine (1.65 ml, 11.9 mmol) in DMSO (10 ml) is added neopentylamine (0.517 g, 5.93 mmol) at ambient temperature under $N_2$ atmosphere. After being stirred at 80° C. for 3 hours, the reaction mixture is diluted with cold water (50 ml) and 1 N aqueous hydrochloric acid (7.0 ml), and extracted with $CH_2Cl_2$. The extract is washed with brine, dried over $MgSO_4$ and concentrated under reduced pressure to give the crude product. Rf=0.27 (AcOEt:MEOH=10:1). $^1$H NMR (400 MHz, DMSO-$d_6$) δ 0.93(s, 9H), 3.31(d, 2H), 8.58(s, 1H), 8.77(br, 1H).

B. 2-Cyano-4-(2,2-dimethyl-propylamino)-pyrimidine-5-carboxylic acid

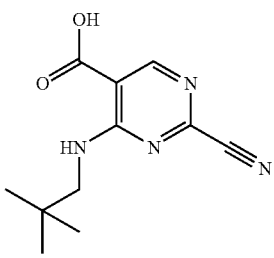

To a solution of NaCN (332 mg, 6.78 mmol) in water (2 ml) and DMSO (8 ml) are added 1,4-diazabicyclo[2,2,2] octane (658 mg, 5.87 mmol) and 2-chloro-4-(2,2-dimethyl-propylamino)-pyrimidine-5-carboxylic acid (1.10 g, 4.52 mmol) successively at ambient temperature. After being stirred for 1 hours at 70° C., the reaction mixture is diluted with cold water (50 ml) and 1 N aqueous hydrochloric acid (11.7 ml), and extracted with $CH_2Cl_2$. The extract is washed with brine, dried over $MgSO_4$ and concentrated under reduced pressure to give the crude product. Rf=0.22 (AcOEt:MEOH=10:1). $^1$H NMR (400 MHz, DMSO-$d_6$) δ 0.94(s, 9H), 3.34(d, 2H), 8.73(s, 1H), 8.94(br, 1H).

C. 2-Cyano-4-(2,2-dimethyl-propylamino)-pyrimidine-5-carboxylic acid (5-methyl-2-phenyl-2H-pyrazol-3-yl)-amide

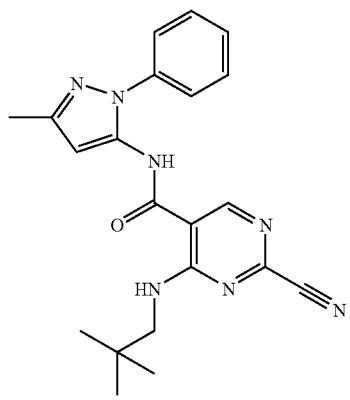

To a solution of 2-Cyano-4-(2,2-dimethyl-propylamino)-pyrimidine-5-carboxylic acid (150 mg, 0.640 mmol), 5-Methyl-2-phenyl-2H-pyrazol-3-ylamine (211 mg, 1.28 mmol) and 1-hydroxybenzotriazole (147 mg, 1.28 mmol) in DMF (5 ml) is added 1-ethyl-3-(3-dimethylaminopropyl)-carbodiimide (199 mg, 1.28 mmol) at ambient temperature. After being stirred for 15 hours at ambient temperature, the reaction mixture is diluted with ethyl acetate, washed with saturated $NaHCO_3$, dried over $MgSO_4$ and concentrated. The crude product is purified by reverse-phase HPLC to give the product. Rf=0.44 (n-hexane:AcOEt=1:1). $^1$H NMR (400 MHz, CDCl$_3$) δ 0.98(s, 9H), 2.33(s, 3H), 3.37(d, 2H), 6.55(s, 1H), 7.41-7.53(m,5H), 8.24(s, 1H), 9.01(br, 1H).

By repeating the procedures described above using appropriate starting materials and conditions the following compounds of formula XI are obtained as identified below in Table 2.

TABLE 2

XI (structure: pyrimidine with 2-cyano, 4-(neopentylamino), 5-C(=O)NH-R)

| Example No. | R-NH- group | Yield(%) | Rf(solvent) | ¹H NMR(400MHz, δ) |
|---|---|---|---|---|
| II-3 | 4-Cl-C₆H₄-CH₂-NH- | 56 | 0.63 (n-hexane:AcOEt=1:1) | (CDCl₃) 1.00(s, 9H), 3.37(d, 2H), 4.57(d, 2H), 6.61(br, 1H), 7.27(d, 2H), 7.33(d, 2H), 8.32(s, 1H), 9.05(br, 1H) |
| II-4 | 4-(Me₂N)-C₆H₄-CH₂-NH- | 47 | 0.54 (n-hexane:AcOEt=1:1) | (CDCl₃) 1.00(s, 9H), 2.95(s, 6H), 3.36(d, 2H), 4.47(d, 2H), 6.37(br, 1H), 6.70(d, 2H), 7.19(d, 2H), 8.25(s, 1H), 9.11(br, 1H) |
| II-5 | C₆H₅-CH₂-NH- | 27 | 0.64 (n-hexane:AcOEt=1:1) | (CDCl₃) 1.00(s, 9H), 3.38(d, 2H), 4.61(d, 2H), 6.38(br, 1H), 7.32–7.38(m, 5H), 8.30(s, 1H), 9.07(br, 1H) |
| II-2 | 3-methyl-1-phenyl-1H-pyrazol-5-yl-NH- | 34 | 0.44 (n-hexane:AcOEt=1:1) | (CDCl₃) 0.98(s, 9H), 2.33(s, 3H), 3.37(d, 2H), 6.55(s, 1H), 7.41–7.53(m, 5H), 8.24(s, 1H), 9.01(br, 1H) |
| II-6 | 1-phenyl-1H-pyrazol-5-yl-NH- | 27 | 0.40 (n-hexane:AcOEt=1:1) | (CDCl₃) 0.99(s, 9H), 3.39(d, 2H), 6.77(d, 1H), 7.47–7.58(m, 5H), 7.68(d, 1H), 8.24(s, 1H), 8.97(br, 1H) |
| II-7 | 2-biphenyl-NH- | 26 | 0.73 (n-hexane:AcOEt=1:1) | (CDCl₃) 1.00(s, 9H), 3.38(d, 2H), 7.28–7.54(m, 8H), 7.86(brs, 1H), 7.91(s, 1H), 8.31(d, 1H), 9.05(br, 1H) |

TABLE 2-continued

XI

| Example No. | R–NH (structure) | Yield(%) | Rf(solvent) | ¹H NMR(400MHz, δ) |
|---|---|---|---|---|
| II-8 | 2-(pyrrol-1-yl)phenyl-NHCH₃ | 22 | 0.67 (n-hexane:AcOEt=1:1) | (CDCl₃) 1.00(s, 9H), 3.38(d, 2H), 6.47–6.49(m, 2H), 6.81–6.82(m, 2H), 7.26–7.29(m, 1H), 7.40–7.43(m, 1H), 7.45–7.49(m, 1H), 7.59(brs, 1H), 7.93(s, 1H), 8.42(d, 1H), 9.05(br, 1H) |
| II-9 | 1-(4-chlorophenyl)-3-methyl-5-(methylamino)pyrazole | 22 | 0.46 (n-hexane:AcOEt=1:1) | (CDCl₃) 0.97(s, 9H), 2.32(s, 3H), 3.37(d, 2H), 6.46(s, 1H), 7.38(d, 2H), 7.44(d, 2H), 8.32(s, 1H), 8.93(br, 1H) |
| II-10 | 1-(2-chlorophenyl)-3-methyl-5-(methylamino)pyrazole | 23 | 0.37 (n-hexane:AcOEt=1:1) | (CDCl₃) 0.98(s, 9H), 2.31(s, 3H), 3.37(d, 2H), 6.48(s, 1H), 7.30–7.42(m, 3H), 7.49(m, 1H), 8.31(s, 1H), 8.91(br, 1H) |
| II-11 | 1-(2,4-dichlorophenyl)-3-methyl-5-(methylamino)pyrazole | 10 | 0.50 (n-hexane:AcOEt=1:1) | (CDCl₃) 0.97(s, 9H), 2.34(s, 3H), 3.35(d, 2H), 6.48(s, 1H), 7.38–7.45(m, 2H), 7.56(m, 1H), 7.83(br, 1H), 8.37(s, 1H), 8.81(br, 1H) |

| Ex | R | MS (ES+) (M+H)⁺ | 1H-NMR |
|---|---|---|---|
| II-12 2-Cyano-4-(2,2-dimethyl-propylamino)-pyrimidine-5-carboxylic acid [2-(4-methoxy-phenyl)-1,1-dimethyl-ethyl]-amide | 4-methoxyphenyl-CH₂-C(CH₃)₂– | 396 | (300MHz, CDCl₃): 8.92(t, 1H), 8.21(s, 1H), 7.03(d, 2H), 6.82(d, 2H), 5.67(s, 1H), 3.79(s, 3H), 3.38(d, 2H), 3.22(s, 2H), 1.45(s, 6H), 1.00(s, 9H). |

-continued

| Ex | R | MS (ES+) (M+H)+ | 1H-NMR |
|---|---|---|---|
| II-13 2-Cyano-4-(2,2-dimethyl-propylamino)-pyrimidine-5-carboxylic acid {1,1-dimethyl-2-[3-(4-methyl-piperazin-1-yl)-phenyl]-ethyl}-amide | | 464 | (300MHz, CDCl$_3$): 8.97(t, 1H), 8.20(s, 1H), 7.40(s, 1H), 7.18(t, 1H), 6.80(m, 1H), 6.68–6.60 (m, 2H), 3.37(d, 2H), 3.16(m, 4H), 3.02(s, 2H), 2.58(m, 4H), 2.39 (s, 3H), 1.48(s, 6H), 1.00 (s, 9H). |
| II-14 2-Cyano-4-(2,2-dimethyl-propylamino)-pyrimidine-5-carboxylic acid {1,1-dimethyl-2-[4-(4-methyl-piperazin-1-yl)-phenyl]-ethyl}-amide | | 464 | (300MHz, CDCl$_3$): 8.92(t, 1H), 8.04(s, 1H), 7.02(d, 2H), 6.84(d, 2H), 5.71(s, 1H), 3.38 (d, 2H), 3.20(m, 4H), 2.98(s, 2H), 2.60(m, 4H), 2.36(s, 3H), 1.45(s, 6H), 1.00(s, 9H). |
| II-15 2-Cyano-4-(2,2-dimethyl-propylamino)-pyrimidine-5-carboxylic acid {1,1-dimethyl-2-[3-(2-pyrrolidin-1-yl-ethylamino)-phenyl]-ethyl}-amide | | 478 | (300MHz, CDCl$_3$): 8.95(t, 1H), 8.05(s, 1H), 7.10(t, 1H), 6.54–6.40 (m, 3H), 5.93(s, 1H), 3.37(d, 2H), 3.18(t, 2H), 2.94(s, 2H), 2.80(t, 2H), 2.65(m, 4H), 1.84(m, 4H), 1.49(s, 6H), 1.00(s, 9H). |
| II-16 2-Cyano-4-(2,2-dimethyl-propylamino)-pyrimidine-5-carboxylic acid (2-{3-[4-(2-ethoxy-ethyl)-piperazin-1-yl]-phenyl}-1,1-dimethyl-ethyl)-amide | | 522 | (300MHz, CDCl$_3$): 8.96(t, 1H), 8.20(s, 1H), 7.16(t, 1H), 6.80(m, 1H), 6.65–6.58(m, 2H), 5.80(s, 1H), 3.60(t, 2H), 3.52(q, 2H), 3.35(d, 2H), 3.13(m, 4H), 3.01 (s, 2H), 2.65(m, 6H), 1.47(s, 3H), 1.20(t, 3H), 1.00(s, 9H). |
| II-17 2-Cyano-4-(2,2-dimethyl-propylamino)-pyrimidine-5-carboxylic acid [2-(4-difluoromethoxy-phenyl)-ethyl]-amide | | 404 | (300MHz, CDCl$_3$): 9.00(t, 1H), 8.18(s, 1H), 7.21(d, 2H), 7.08(d, 2H), 6.14(t, 1H), 3.68 (m, 2H), 3.36(d, 2H), 2.93(t, 2H), 1.00(s, 9H). |
| II-18 2-Cyano-4-(2,2-dimethyl-propylamino)-pyrimidine-5-carboxylic acid {2-[3-(4-methyl-piperazin-1-yl)-phenyl]-ethyl}-amide | | 436 | (400MHz, DMSO-d6): 9.28(t, 1H), 8.92(t, 1H), 7.21(t, 1H), 6.78(s, 1H), 6.76(d, 1H), 6.64(d, 1H), 3.49(q, 2H), 3.30(d, 2H), 3.11(m, 4H), 2.78 (t, 2H), 2.48(m, 4H), 2.22(s, 3H), 0.98(s, 9H). |

The invention claimed is:

1. A compound of formula I, or a pharmaceutically acceptable salt thereof

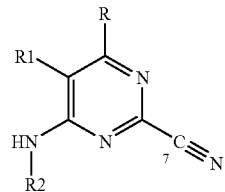

I wherein

R is H, —R4, —OR4 or NR3R4, wherein R3 is H, lower alkyl or $C_3$ to $C_{10}$ cycloalkyl, and R4 is lower alkyl or $C_3$ to $C_{10}$ cycloalkyl, wherein R3 and R4 are independently, optionally substituted by halo, hydroxy, lower alkoxy, CN, $NO_2$, or optionally mono- or di-lower alkyl substituted amino;

R1 is —CO—NR5R6, —NH—CO—R5, —CH$_2$—NH—C(O)—R5, —CO—R5, —S(O)—R5, —S(O)$_2$—R5, —CH$_2$—CO—R5 or —CH$_2$—NR5R6, wherein R5 is aryl, aryl-lower alkyl, $C_3$–$C_{10}$cycloalkyl, $C_3$–$C_{10}$cycloalkyl-lower alkyl, heterocyclyl or heterocyclyl-lower alkyl, R6 is H, aryl, aryl-lower alkyl, aryl-lower-alkenyl, $C_3$–$C_{10}$cycloalkyl, $C_3$–$C_{10}$cycloalkyl-lower alkyl, heterocyclyl or heterocyclyl-lower alkyl, or wherein R5 and R6 together with the nitrogen atom to which they attached are joined to form an N-heterocyclyl group, wherein N-heterocyclyl denotes a saturated, partially unsaturated or aromatic nitrogen containing heterocyclic moiety attached via a nitrogen atom thereof having from 3 to 8 ring atoms optionally containing a further 1, 2 or 3 heteroatoms selected from N, NR7, O, S, S(O) or S(O)$_2$ wherein R7 is H or optionally substituted lower alkyl, carboxy, acyl, amido, aryl, S(O) or S(O)$_2$, and wherein the N-heterocyclyl is optionally fused in a bicyclic structure, and wherein the N-heterocyclyl is optionally linked in a spiro structure with a 3 to 8 membered cycloalkyl or heterocyclic ring wherein the heterocyclic ring has from 3 to 10 ring members and contains from 1 to 3 heteroatoms selected from N, NR6, O, S, S(O) or S(O)$_2$ wherein R6 is as defined above, and wherein heterocyclyl denotes a ring having from 3 to 10 ring members and containing from 1 to 3 heteroatoms selected from N, NR7, O, S, S(O) or S(O)$_2$ wherein R7 is as defined above, and wherein R5 and R6 are independently, optionally substituted by one or more groups, selected from halo, hydroxy, oxo, lower alkoxy, CN and $NO_2$, or optionally substituted by mono- or di-lower alkyl substituted amino, lower alkoxy, aryl, aryl-lower alkyl, N-heterocyclyl or N-heterocyclyl-lower alkyl wherein the optional substitution consists of from 1 to 3 substituents selected from halo, hydroxy, lower alkoxy, lower alkoxy-lower alkyl, lower alkoxy-carbonyl CN, and $NO_2$, R2 is is independently H, or optionally substituted with lower alkyl, aryl, aryl-lower alkyl, $C_3$–$C_{10}$cycloalkyl, $C_3$–$C_{10}$cycloalkyl-lower alkyl, heterocyclyl or heterocyclyl-lower alkyl, and wherein R2 is optionally substituted by halo, hydroxy, oxo, lower alkoxy, CN, $NO_2$, or optionally mono- or di-lower alkyl substituted amino.

2. A compound according to claim 1 of formula II, or a pharmaceutically acceptable salt thereof

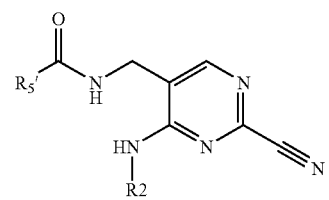

II wherein R2 is as defined above and R5' is as defined above for R5 in claim 1.

3. A compound according to claim 1 of formula IIa, or a pharmaceutically acceptable salt thereof

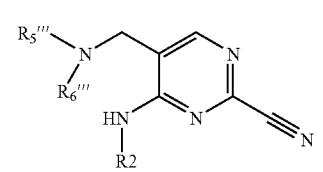

IIa wherein R2 is as defined above and R5''' and R6''' is as defined above for R5 and R6 respectively in claim 1.

4. A compound according to claim 1 of formula III or a pharmaceutically acceptable salt thereof

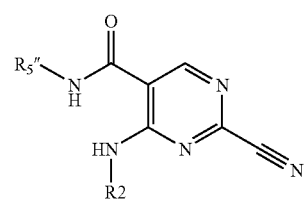

III wherein R2 is as defined above and R5'' is as defined above for R5 in claim 1.

5. A pharmaceutical composition comprising a compound according to claim 1 as an active ingredient.

6. A method of treating a patient suffering from a disease selected from osteoarthritis, rheumatoid arthritis, and osteoporosis, comprising administering an effective amount of a compound according to claim 1 to the patient.

7. A process for the preparation of a compound of Formula II or a pharmaceutically acceptable salt thereof

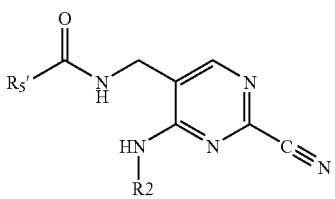

wherein R2 is optionally substituted with lower alkyl, aryl, aryl-lower alkyl, $C_3$–$C_{10}$cycloalkyl, $C_3$–$C_{10}$cycloalkyl-lower alkyl, heterocyclyl or heterocyclyl-lower alkyl halo, hydroxy, oxo, lower alkoxy, CN, $NO_2$, or mono- or di-lower alkyl substituted amino, wherein R5' is aryl, aryl-lower alkyl, $C_3$–$C_{10}$cycloalkyl, $C_3$–$C_{10}$cycloalkyl-lower alkyl, heterocyclyl or heterocyclyl-lower alkyl, oxo, mono- or di-lower alkyl substituted amino, lower alkoxy, aryl, aryl-lower alkyl, N-heterocyclyl or N-heterocyclyl-lower alkyl or from 1 to 3 substituents selected from the group comprising halo, hydroxy, lower alkoxy-lower alkyl, lower alkoxy-carbonyl, CN, and $NO_2$, comprising cyanation of a 2-chloro precursor of formula IV

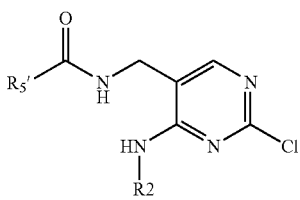

wherein R2 and R5' are as defined above, and thereafter, optionally, converting the product obtained into a further compound of formula II, or into a salt thereof.

8. A process for the preparation of a compound of Formula IIa or a pharmaceutically acceptable salt thereof

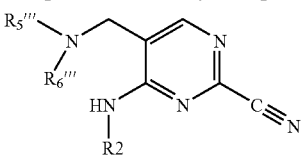

wherein R2 is defined as in claim 7, R5''' is defined above for R5' in claim 7 and R6''' is H, aryl, aryl-lower alkyl, aryl-lower-alkenyl, $C_3$–$C_{10}$cycloalkyl, $C_3$–$C_{10}$cycloalkyl-lower alkyl, heterocyclyl or heterocyclyl-lower alkyl, or wherein R5''' and R6''' together with the nitrogen atom to which they attached are joined to form an N-heterocyclyl group, wherein N-heterocyclyl denotes a saturated, partially unsaturated or aromatic nitrogen containing heterocyclic moiety attached via a nitrogen atom thereof having from 3 to 8 ring atoms optionally containing a further 1, 2 or 3 heteroatoms selected from N, NR7, O, S, S(O) or $S(O)_2$ wherein R7 is H or optionally substituted with a lower alkyl, carboxy, acyl amido, aryl, S(O) or $S(O)_2$, and wherein the N-heterocyclyl is optionally fused in a bicyclic structure, and wherein the N-heterocyclyl is optionally linked in a spiro structure with a 3 to 8 membered cycloalkyl or heterocyclic ring wherein the heterocyclic ring has from 3 to 10 ring members and contains from 1 to 3 heteroatoms selected from N, NR6, O, S, S(O) or $S(O)_2$ wherein R6''' is as defined above, and wherein heterocyclyl denotes a ring having from 3 to 10 ring members and containing from 1 to 3 heteroatoms selected from N, NR7, O, S, S(O) or $S(O)_2$ wherein R7 is as defined above, and wherein R5''' and R6''' are independently, optionally, substituted by one or more groups, selected from the group comprising halo, hydroxy, oxo, lower alkoxy, CN and $NO_2$, or optionally substituted with mono- or di-lower alkyl substituted amino, lower alkoxy, aryl, aryl-lower alkyl, N-heterocyclyl or N-heterocyclyl-lower alkyl wherein the optional substitution comprises from 1 to 3 substituents selected from the group comprising halo, hydroxy, lower alkoxy, lower alkoxy-lower alkyl, lower alkoxy-carbonyl CN, and $NO_2$, comprising cyanation of a 2-chloro precursor of formula IVa

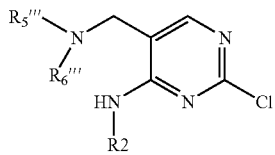

wherein R2, R5''' and R6''' are as defined above, and thereafter, optionally, converting the product obtained into a further compound of formula IIa, or into a salt thereof.

9. A process for the preparation of a compound of Formula III or a pharmaceutically acceptable salt thereof

wherein R2 is as defined above and R5'' is as defined above for R5''' in claim 8, comprising either cyanation of a 2-chloro precursor of formula V or coupling of a carboxylic acid precursor of formula VI with a corresponding amine of formula VII

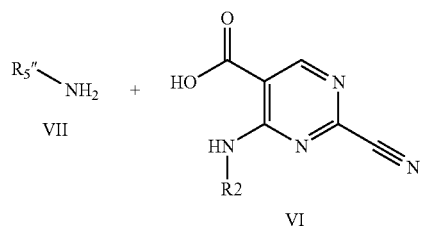
wherein the R2 and R5" of formula V and formula VI are as defined in claim 8, and thereafter, optionally, converting the product obtained into a further compound of formula III, or into a salt thereof.
* * * * *